(12) United States Patent
Jolidon et al.

(10) Patent No.: US 7,964,645 B2
(45) Date of Patent: Jun. 21, 2011

(54) DI-AROMATIC SUBSTITUTED AMIDES AS INHIBITORS FOR GLYT-1

(75) Inventors: Synese Jolidon, Blauen (CH); Robert Narquizian, Saint Louis (FR); Emmanuel Pinard, Linsdorf (FR)

(73) Assignee: Hoffmann-La Roche Inc., Nutley, NJ (US)

(*) Notice: Subject to any disclaimer, the term of this patent is extended or adjusted under 35 U.S.C. 154(b) by 921 days.

(21) Appl. No.: 11/893,932

(22) Filed: Aug. 17, 2007

(65) Prior Publication Data
US 2008/0076806 A1  Mar. 27, 2008

(30) Foreign Application Priority Data
Aug. 21, 2006 (EP) .................... 06119234

(51) Int. Cl.
A61K 31/16 (2006.01)
C07C 233/05 (2006.01)
(52) U.S. Cl. ...................... 514/616; 564/139
(58) Field of Classification Search .......... 514/616; 564/139
See application file for complete search history.

(56) References Cited

U.S. PATENT DOCUMENTS
6,506,782 B1  1/2003  Thorsett

FOREIGN PATENT DOCUMENTS
| EP | 0838471 | 4/1998 |
|----|---------|--------|
| WO | WO 99/55688 | * 11/1991 |
| WO | WO 96/33161 | 10/1996 |
| WO | WO 98/22433 | 5/1998 |
| WO | WO 99/34790 | 7/1999 |
| WO | WO 2006/080477 | 8/2006 |

OTHER PUBLICATIONS

Pacic et al., J. Med. Chem. (2005), vol. 48(2), pp. 475-482; Connor et al.*
Frank et al., Pept. Proc. Am. Pept. Symp., 5th, (1977), pp. 514-517.*
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Pralong, et al., Prog. Neurobiol. 67, pp. 173-202 (2002).
Carlsson M. L., J. Neural Transm. 105, pp. 525-535 (1998).
Armer et al., Exp. Opin. Ther. Patents 11(4) pp. 563-572 (2001).
Baruah et al., Synlett pp. 409-410 (1999).
Laurent et al., Synthesis pp. 667-672 (2000).
Dejaegher et al., Synlett, 1, pp. 113-115 (2002).
Sakaiubara et al., Bulletin of the Chem. Society of Japan vol. 40, No. 9, pp. 2164-2167 (1967).
Steglich et al., Abstract XP-002458221, Pept. Proc. Eur. Pept. Symp. 8th Meeting (1967), pp. 67-72.
Ooi, et al., J. Am. Chem. Soc. vol. 127, No. 14, pp. 5073-5083 (2005).
Conley et al., J. Med. Chem. vol. 30, pp. 567-574 (1987).
Rajic et al., Molecules, vol. 11, No. 11, pp. 837-848 (2006).
Abstract XP-002458222: Enamine Screening Library (2007).

* cited by examiner

*Primary Examiner* — Taofiq A Solola
(74) *Attorney, Agent, or Firm* — George W. Johnston; Patricia S. Rocha-Tramaloni; Kimberly J. Prior

(57) ABSTRACT

The present invention relates to compounds of formula I

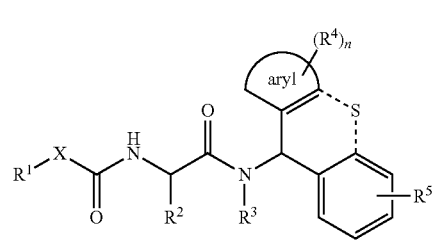

wherein

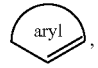

$R^1$,
$R^2, R^3,$
$R^4,$ $R^5$, X, and n are as defined herein and the dotted line denotes an optional bond and pharmaceutically acceptable acid addition salts thereof. The compounds are useful in the treatment of neurological and neuropsychiatric disorders.

14 Claims, No Drawings

DI-AROMATIC SUBSTITUTED AMIDES AS INHIBITORS FOR GLYT-1

PRIORITY TO RELATED APPLICATION(S)

This application claims the benefit of European Patent Application No. 06119234.0, filed Aug. 21, 2006, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, NY; Bliss T V and Collingridge G L, 1993, Nature, 361: 31-39). Transgenic mice overexpressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

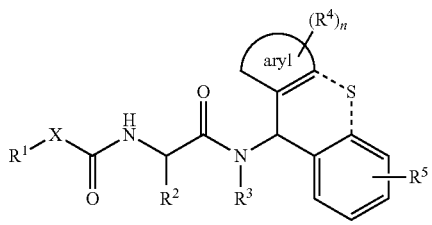

wherein

is a 5 or 6-membered aromatic or heteroaromatic ring;
$R^1$ is cycloalkyl or is aryl or heteroaryl, which is unsubstituted or substituted by 1 to 3 substituents selected from the group consisting of halogen, lower alkyl, lower alkyl substituted by halogen, lower alkoxy, lower alkoxy substituted by halogen, —C(O)-lower alkyl, —S(O)$_2$-lower alkyl, nitro and cyano;
$R^2$ is hydrogen or lower alkyl;
$R^3$ is hydrogen or lower alkyl;
$R^4$ is halogen, lower alkyl, lower alkyl substituted by halogen, lower alkoxy, lower alkoxy substituted by halogen or nitro;
$R^5$ is hydrogen, halogen, lower alkyl or lower alkyl substituted by halogen;
X is a bond, —(CH$_2$)$_m$—, —CH$_2$O— or —CH$_2$NH—;
The dotted line denotes an optional bond;
n is 1 or 2;
m is 1, 2 or 3;
and pharmaceutically acceptable acid addition salts thereof.

Furthermore, the invention includes all racemic mixtures, all their corresponding enantiomers and/or optical isomers.

The present invention also provides pharmaceutical compositions containing compounds of formula I or pharmaceutically acceptable salts thereof. The invention also provides methods for the preparation of the compounds and compositions of the invention.

The compounds of formula I are good inhibitors of the glycine transporter 1 (GlyT-1), and that they have a good selectivity to glycine transporter 2 (GlyT-2) inhibitors. Thus, the present invention provides methods for the treatment of neurological and neuropsychiatric disorders. The present invention provides methods for the treatment of diseases related to activation of NMDA receptors via Glyt-1 inhibition, for example, the treatment of psychoses, disfunction in memory and learning, schizophrenia, dementia and other diseases in which cognitive processes are impaired, such as attention deficit disorders or Alzheimer's disease. The preferred indications of the invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "cycloalkyl" denotes a saturated or partially saturated ring containing from 3 to 7 carbon atoms, for example cyclopropyl, cyclopentyl, cyclopentenyl, cyclohexyl, cyclohexenyl, cycloheptyl or cycloheptenyl.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, having from 6 to 12 ring carbon atoms for example phenyl or naphthyl.

The term "heteroaryl" denotes a cyclic aromatic radical, consisting of one or more fused rings, wherein at least one ring is aromatic in nature and wherein the radical contains 6 to 10 ring atoms, wherein one, two or three of the ring atoms are heteroatoms selected from the group consisting of oxygen, sulphur and nitrogen, for example pyridyl, quinoxalinyl, dihydrobenzofuranyl, thiophenyl, isoxazolyl, pyrazinyl, pyrimidinyl, pyridazinyl, triazinyl, thiazolyl, furyl, pyrrolyl, imidazolyl, pyrazolyl, oxazolyl or isothiazolyl.

The term

is a 5 or 6 membered aromatic or heteroaromatic ring, which denotes a cyclic aromatic radical, optionally containing one, two or three heteroatoms, selected from the group consisting of oxygen, sulphur and nitrogen, for example phenyl, thiophenyl, isothiazolyl, pyridyl or pyridazinyl.

The term "lower alkyl substituted by halogen" denotes a lower alkyl group as defined above, wherein at least one hydrogen atom is replaced by a halogen atom, for example the following groups: CF$_3$, CHF$_2$, CH$_2$F, CH$_2$CF$_3$, CH$_2$CHF$_2$, CH$_2$CH$_2$F, CH$_2$CH$_2$CF$_3$, CH$_2$CH$_2$CH$_2$CF$_3$, CH$_2$CH$_2$Cl, CH$_2$CF$_2$CF$_3$, CH$_2$CF$_2$CHF$_2$, CF$_2$CHFCF$_3$, C(CH$_3$)$_2$CF$_3$, CH(CH$_3$)CF$_3$ or CH(CH$_2$F)CH$_2$F.

The term "lower alkoxy" denotes a lower alkyl group as defined above, which is attached via an oxygen atom.

The term "lower alkoxy substituted by halogen" denotes an alkoxy group as defined above, wherein at least one hydrogen atom is replaced by halogen as defined above.

The term "thiophenyl" is synonymous with thienyl and represents a thiophene substituent, i.e., C$_4$H$_4$S.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of formula I

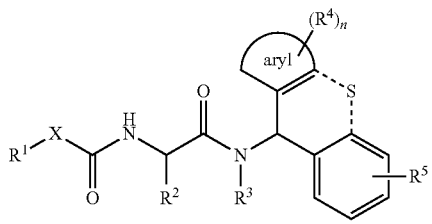

wherein

is a 5 or 6-membered aromatic or heteroaromatic ring;
R¹ is cycloalkyl or is aryl or heteroaryl, which is unsubstituted or substituted by 1 to 3 substituents selected from the group consisting of halogen, lower alkyl, lower alkyl substituted by halogen, lower alkoxy, lower alkoxy substituted by halogen, —C(O)-lower alkyl,
—S(O)₂-lower alkyl, nitro and cyano;
R² is hydrogen or lower alkyl;
R³ is hydrogen or lower alkyl;
R⁴ is halogen, lower alkyl, lower alkyl substituted by halogen, lower alkoxy, lower alkoxy substituted by halogen or nitro;
R⁵ is hydrogen, halogen, lower alkyl or lower alkyl substituted by halogen;
X is a bond, —(CH₂)ₘ—, —CH₂O— or —CH₂NH—;
The dotted line denotes an optional bond;
n is 1 or 2;
m is 1, 2 or 3;
and pharmaceutically acceptable acid addition salts thereof.

Furthermore, the invention includes all racemic mixtures, all their corresponding enantiomers and/or optical isomers.

Preferred compounds of formula I of the present invention are those, wherein

is a 6-membered aromatic group, preferentially phenyl, monosubstituted by halogen, lower alkyl substituted by halogen or by lower alkyl, R³ and R⁴ are preferentially hydrogen, X is preferentially a bond and R¹ is preferentially an aryl group, unsubstituted or substituted by fluoro, cyano or nitro. Such compounds are for example
rac-N-({[(4-chloro-phenyl)-phenyl-methyl]-carbamoyl}-methyl)-4-fluoro-benzamide
rac-N-({[phenyl-(3-trifluoromethyl-phenyl)-methyl]-carbamoyl}-methyl)-benzamide
rac-4-fluoro-N-({[phenyl-(3-trifluoromethyl-phenyl)-methyl]-carbamoyl}-methyl)-benzamide
rac-4-cyano-N-({[phenyl-(3-trifluoromethyl-phenyl)-methyl]-carbamoyl}-methyl)-benzamide
N-[(benzhydryl-carbamoyl)-methyl]-4-fluoro-benzamide
rac-N-({[(3-chloro-phenyl)-phenyl-methyl]-carbamoyl}-methyl)-4-fluoro-benzamide
rac-4-fluoro-N-{[(phenyl-m-tolyl-methyl)-carbamoyl]-methyl}-benzamide
rac-4-fluoro-N-({[(4-fluoro-phenyl)-phenyl-methyl]-carbamoyl}-methyl)-benzamide
N-({[bis-(3-fluoro-phenyl)-methyl]-carbamoyl}-methyl)-4-fluoro-benzamide
rac-N-({[(3,5-difluoro-phenyl)-phenyl-methyl]-carbamoyl}-methyl)-4-fluoro-benzamide
rac-N-({[(4-chloro-phenyl)-(3-trifluoromethyl-phenyl)-methyl]-carbamoyl}-methyl)-4-fluoro-benzamide
rac-4-fluoro-N-({[(4-fluoro-phenyl)-(3-trifluoromethyl-phenyl)-methyl]-carbamoyl}-methyl)-benzamide
rac-4-fluoro-N-({[(3-fluoro-phenyl)-(3-trifluoromethyl-phenyl)-methyl]-carbamoyl}-methyl)-benzamide
rac-4-fluoro-N-({[p-tolyl-(3-trifluoromethyl-phenyl)-methyl]-carbamoyl}-methyl)-benzamide
5-methyl-thiophene-2-carboxylic acid ({[bis-(3-fluoro-phenyl)-methyl]-carbamoyl}-methyl)-amide and
N-({[bis-(3-fluoro-phenyl)-methyl]-carbamoyl}-methyl)-4-nitro-benzamide.

Preferred compounds of formula I of the present invention are further those, wherein

is a 6-membered aromatic group, preferentially phenyl, monosubstituted by halogen, R³ and R⁴ are preferentially hydrogen, X is preferentially a bond and R¹ is preferentially heteroaryl, unsubstituted or substituted by nitro. Such compounds are for example
rac-5-nitro-thiophene-2-carboxylic acid ({[(4-chloro-phenyl)-phenyl-methyl]-carbamoyl}-methyl)-amide
rac-thiophene-3-carboxylic acid ({[(4-chloro-phenyl)-phenyl-methyl]-carbamoyl}-methyl)-amide
5-nitro-thiophene-2-carboxylic acid ({[bis-(3-fluoro-phenyl)-methyl]-carbamoyl}-methyl)-amide and
thiophene-3-carboxylic acid ({[bis-(3-fluoro-phenyl)-methyl]-carbamoyl}-methyl)-amide.

A further embodiment of the invention are compounds of formula I, wherein X is —(CH₂)ₘ— or —CH₂O— or —CH₂NH— and the other definitions are as described above.
The invention provides compounds of formula I in which n is 1. The invention also provides compounds of formula I in which wherein the dotted line is not a bond. The invention further provides compounds of formula I wherein

is phenyl, unsubstituted or substituted by 1 to 3 substituents selected from the group consisting of halogen, lower alkyl, and lower alkyl substituted by halogen.

The present invention provides compounds of formula I in which X is a bond,

is phenyl, unsubstituted or substituted by 1 to 3 substituents selected from the group consisting of halogen, lower alkyl, lower alkyl substituted by halogen, lower alkoxy, lower alkoxy substituted by halogen, C(O)-lower alkyl, S(O)$_2$-lower alkyl, nitro, and cyano; and n is 1. The invention also provides compounds of formula I in which R$^3$ is H. Alternatively, the invention provides compounds of formula I in which R$^3$ is methyl.

The present compounds of formula I and their pharmaceutically acceptable salts can be prepared by methods known in the art, for example, by processes described below, which processes comprise a) reacting a compound of formula II

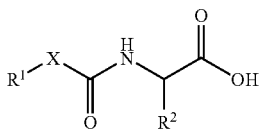

with a compound of formula

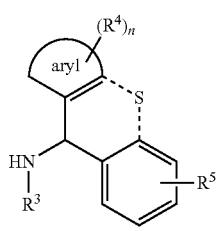

in the presence of an activating agent, such as TBTU (2-(1H-benzotriazole-1-yl)-1,1,3,3-tetramethyluroniumtetrafluoroborate), DCC N,N'-dicyclohexylcarbodiimide or EDCI 1-(3-dimethylaminopropyl)-3-ethylcarbodiimide, to obtain a compound of formula

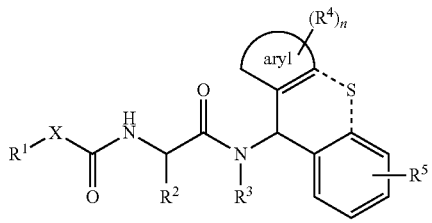

wherein the substituents are as defined above, or b) reacting a compound of formula

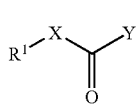

for X=—(CH$_2$)$_n$—
with a compound of formula

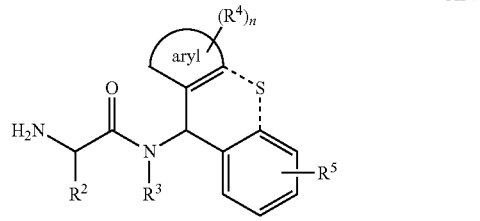

in presence of a coupling reagent, like TBTU, DCC or EDCI, or with an acid halide to obtain a compound of formula

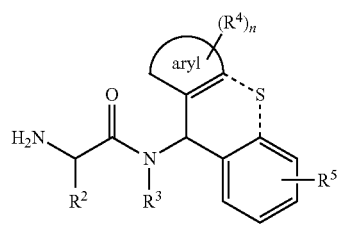

wherein the substituents are as defined above and Y is halogen or hydroxy, or c) reacting a compound of formula

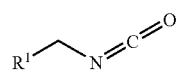

for X=—CH$_2$NH—
with a compound of formula

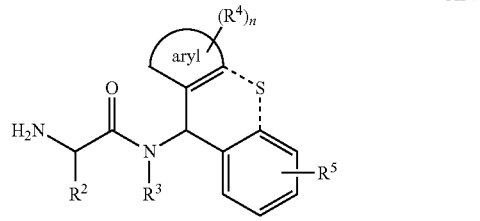

to obtain a compound of formula

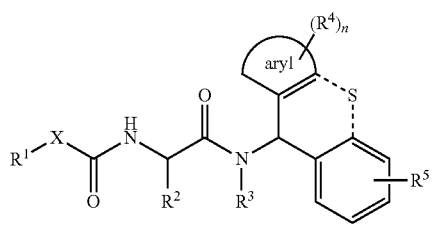

wherein the substituents are as defined above.
and if desired, converting the compounds obtained into pharmaceutically acceptable acid addition salts.

The acid addition salts of the basic compounds of formula I can be converted to the corresponding free bases by treatment with at least a stoichiometric equivalent of a suitable base, such as sodium or potassium hydroxide, potassium carbonate, sodium bicarbonate, ammonia, and the like.

The compounds of formula I can be prepared in accordance with process variant a) to c), with the following schemes 1 to 7, and with working examples 1.1-1.98.

The starting material is commercially available or can be prepared in accordance with known methods.

The following abbreviations have been used in the schemes and examples:
TBTU=(2-(1H-benzotriazole-1-yl)-1,1,3,3-tetramethyluroniumtetrafluoroborate)
DCC=N,N'-dicyclohexylcarbodiimide
EDCI=1-(3-dimethylaminopropyl)-3-ethylcarbodiimide
DIPEA=ethyl-diisopropyl-amine Scheme 1 shows the preparation of compounds of formula I by reacting a compound of formula II with a compound of formula III, which reaction can be carried out in the presence of an activating agent such as TBTU, DCC or EDCI.

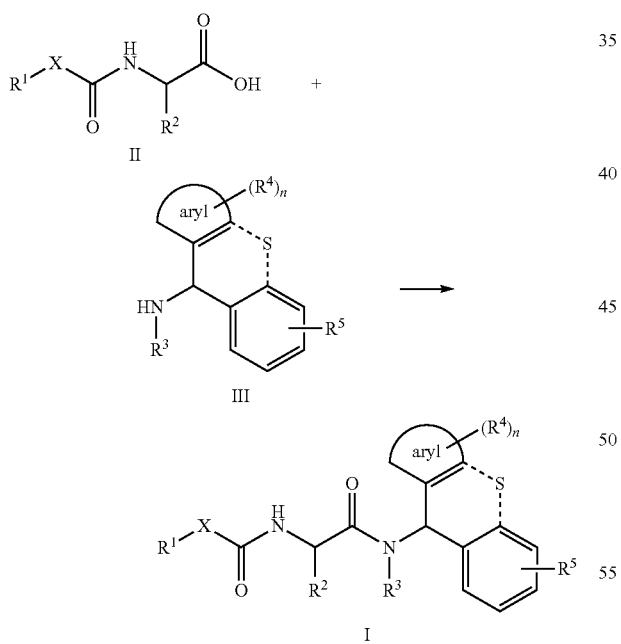

Compounds of the formula II are either commercially available, their preparation is described in the chemical literature or they can be prepared by methods known in the art, for example by coupling glycine or serine with an organic acid in presence of an activating agent like TBTU, DCC or EDCI (when $X=(CH_2)_m$) or by coupling glycine or serine with an isocyanate (when $X=CH_2NH$).

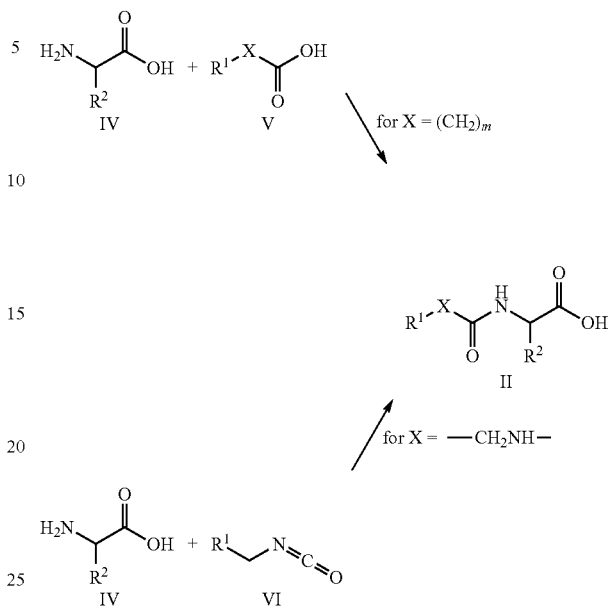

Compounds of the formula III are either commercially available, their preparation is described in the chemical literature or they can be prepared by methods known in the art. These methods include:

Reducing ketimines or oximes, as described for example by Baruah et al., Synlett 1999, 409.

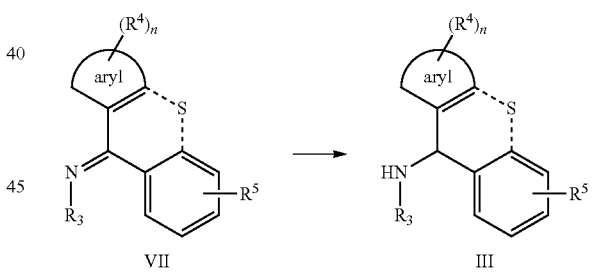

Reacting a secondary alcohol with phenylcarbamate and deprotecting the intermediate carbamate, as described by Laurent et al., Synthesis 2000, 667.

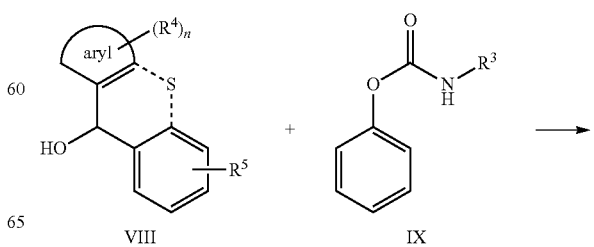

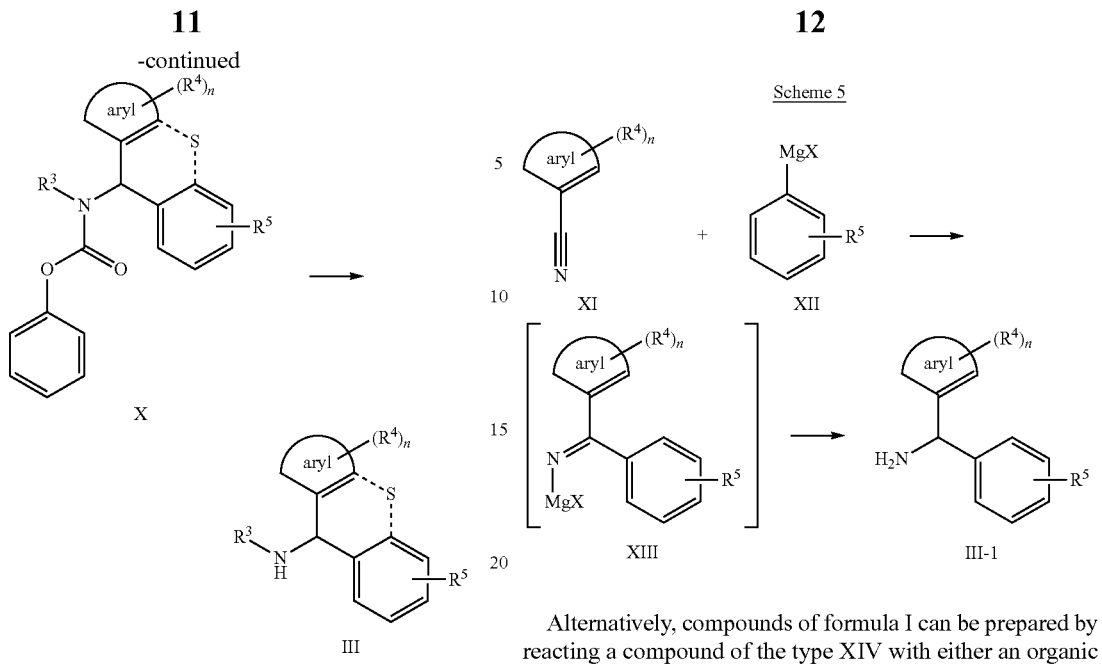

Adding a Grignard-reagent to a nitrile and reducing the intermediate imine with sodium borohydride, as described by Dejaegher et al, Synlett 2002, 113.

Alternatively, compounds of formula I can be prepared by reacting a compound of the type XIV with either an organic acid in presence of a coupling reagent like TBTU, DCC or EDCI or with an acid halide (when X is —$(CH_2)_n$—) or reacting compound XIV with an isocyanate (when X=—$CH_2NH$—)

Scheme 6

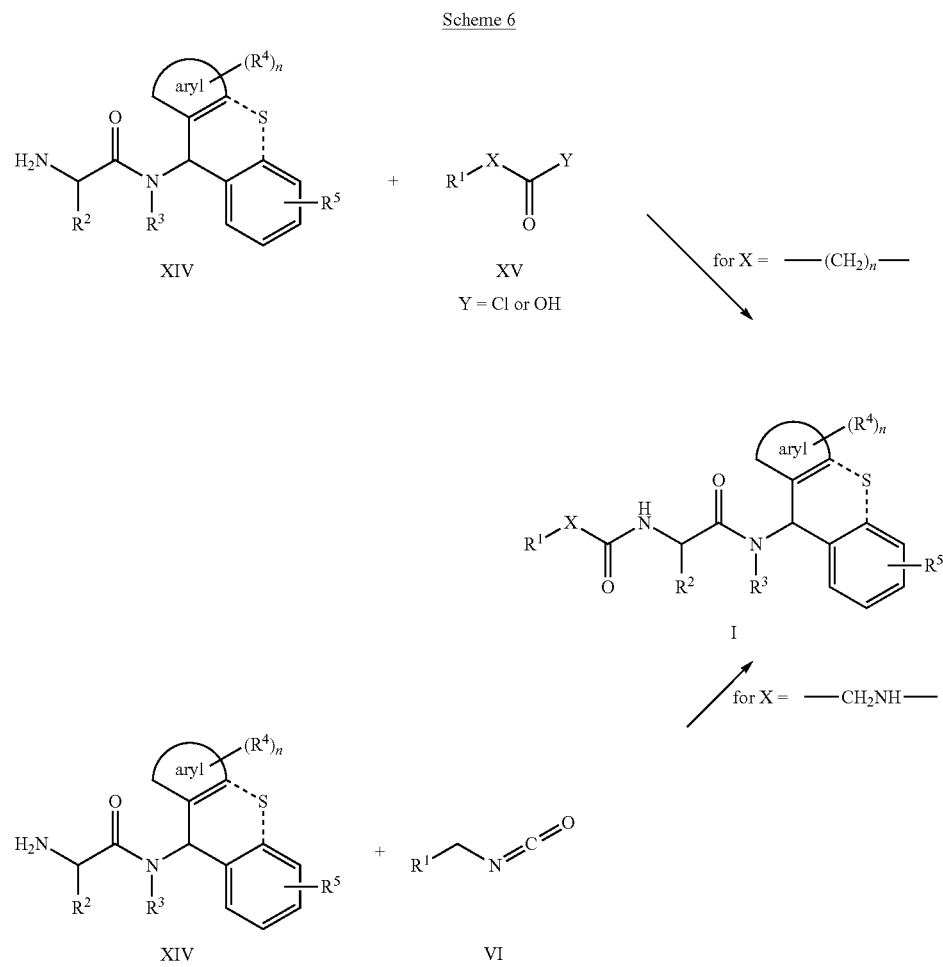

Compounds XIV can be prepared by reacting an N-protected glycine or serine-derivative with a compound of the type III. The protecting group, which is for example BOC (N-tert.butyloxycarbonyl) is then removed by known procedures.

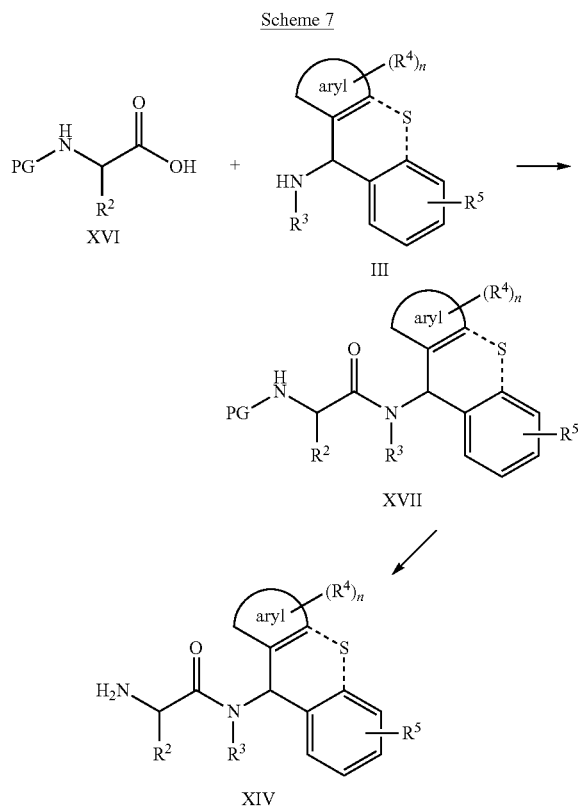

Scheme 7

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The following $IC_{50}$ data (<0.1 μM) for representative compounds may be provided:

| Example No. | GlyT-1 $IC_{50}$ |
|---|---|
| 1.29 | 0.088 |
| 1.30 | 0.054 |
| 1.32 | 0.015 |
| 1.34 | 0.089 |
| 1.43 | 0.025 |
| 1.44 | 0.019 |
| 1.47 | 0.092 |
| 1.63 | 0.033 |
| 1.67 | 0.056 |
| 1.69 | 0.088 |
| 1.70 | 0.016 |
| 1.72 | 0.025 |
| 1.76 | 0.074 |
| 1.77 | 0.048 |
| 1.78 | 0.058 |
| 1.86 | 0.042 |
| 1.99 | 0.090 |
| 1.98 | 0.028 |
| 1.99 | 0.075 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants.

They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease. Therefore, the present invention provides a method for the treatment of schizophrenia which comprises administering to an individual a therapeutically effective amount of a compound of formula I or a pharmaceutically acceptable salt thereof. The invention also provides a method for the treatment of Alzheimer's disease which comprises administering to an individual a therapeutically effective amount of a compound of formula I or a pharmaceutically acceptable salt thereof. The invention further provides a method for improving cognition which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/ capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the present invention without limiting it. All temperatures are given in degree Celsius.

Example 1.1

Preparation of N-[(Benzhydryl-methyl-carbamoyl)-methyl]-3-phenyl-propionamide

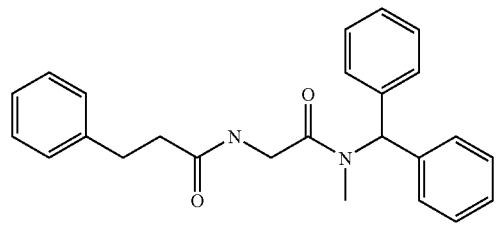

A solution of 2.0 mmol N-(diphenylmethyl)methylamine, 2.0 mmol (3-phenyl-propionylamino)-acetic acid (CA [56613-60-6]) and 6.0 mmol DIPEA in 10 ml of acetonitrile was treated with 2.2 mmol of TBTU. After 2 hours at room temperature, the reaction mixture was concentrated, diluted with water and extracted 3 times with ethyl acetate. The organic phase was dried and the residue purified by chromatography (SiO$_2$; dichloromethane/methanol) to give the title compound as a slightly yellowish solid.

Yield=46%. MS (m/e): 385.2 (MH$^-$, 100%).

Example 1.2

Preparation of rac-N-[(2-Chloro-9H-thioxanthen-9-ylcarbamoyl)-methyl]-3-phenyl-propionamide

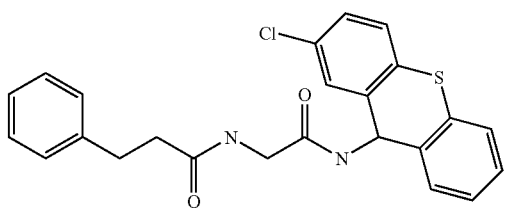

Prepared in analogy to example 1.1 from rac-2-chloro-9H-thioxanthen-9-ylamine (CA [51065-24-8]) and (3-phenyl-propionylamino)-acetic acid (CA [56613-60-6]).
MS (m/e): 435.2 (MH⁻, 100%).

Example 1.3

Preparation of rac-N-({[(4-Chloro-phenyl)-phenyl-methyl]-carbamoyl}-methyl)-benzamide

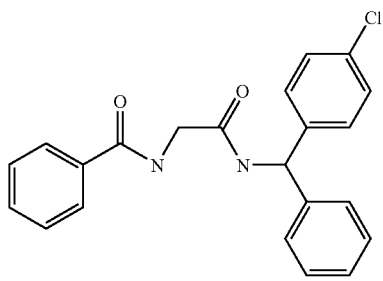

Prepared in analogy to example 1.1 from rac-4-chlorobenzhydrylamine hydrochloride and hippuric acid.
MS (m/e): 377.3 (MH⁻, 100%).

Example 1.4

Preparation of rac-({[(4-Chloro-phenyl)-phenyl-methyl]-carbamoyl}-methyl)-carbamic acid benzyl ester

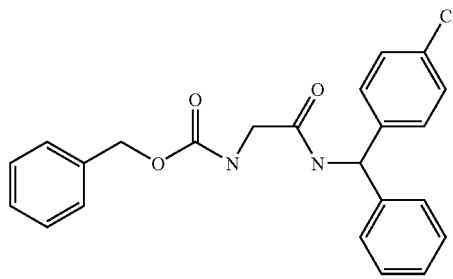

Prepared in analogy to example 1.1 from rac-4-chlorobenzhydrylamine hydrochloride and benzyloxycarbonylamino-acetic acid (CA [1138-80-3]).
MS (m/e): 409.3 (M+H⁺; 45%).

Example 1.5

Preparation of rac-(N-({[(4-Chloro-phenyl)-phenyl-methyl]-methyl-carbamoyl}-methyl)-3-phenyl-propionamide

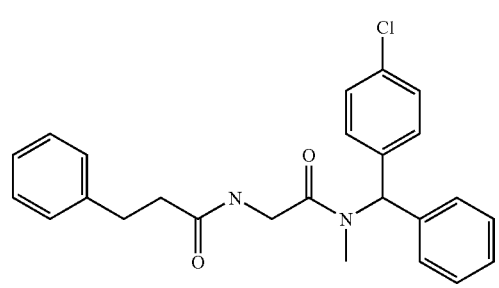

Prepared in analogy to example 1.1 from rac-[(4-chloro-phenyl)-phenyl-methyl]-methylamine (CA [118762-04-2]) and (3-phenyl-propionylamino)-acetic acid (CA [56613-60-6]).
MS (m/e): 419.3 (MH⁻, 100%).

Example 1.6

Preparation of rac-N-({[(4-Chloro-phenyl)-phenyl-methyl]-carbamoyl}-methyl)-2-phenyl-acetamide

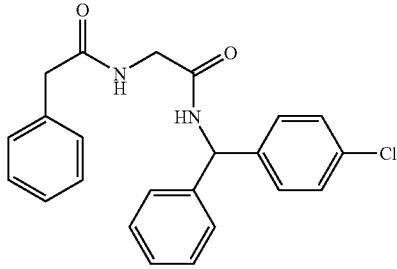

Prepared in analogy to example 1.1 from rac-4-chlorobenzhydrylamine hydrochloride and phenylacetylamino-acetic acid (CA [500-98-1]).
MS (m/e): 391.2 (MH⁻, 100%).

Example 1.7

Preparation of rac-3-(4-Chloro-phenyl)-N-({[(4-chloro-phenyl)-phenyl-methyl]-carbamoyl}-methyl)-propionamide

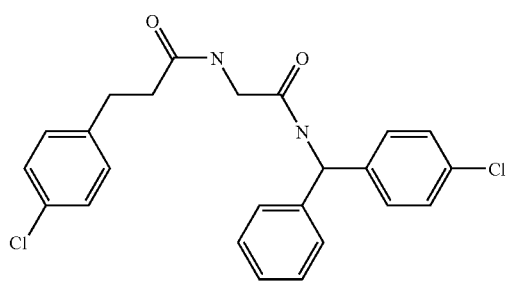

Prepared in analogy to example 1.1 from rac-4-chlorobenzhydrylamine hydrochloride and [3-(4-chloro-phenyl)-propionylamino]-acetic acid (Example 2.1).
MS (m/e): 439.3 (MH⁻, 100%).

Example 1.8

Preparation of rac-N-({[(4-Chloro-phenyl)-phenyl-methyl]-carbamoyl}-methyl)-3-(4-methoxy-phenyl)-propionamide

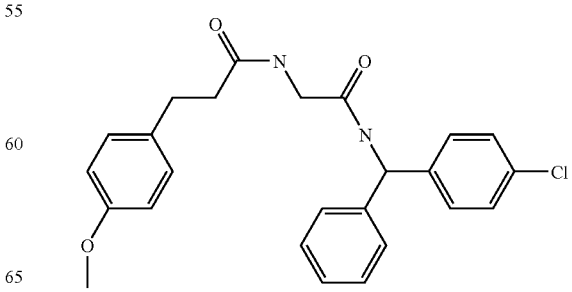

Prepared in analogy to example 1.1 from rac-4-chlorobenzhydrylamine hydrochloride and [3-(4-methoxy-phenyl)-propionylamino]-acetic acid (Example 2.2).

MS (m/e): 435.2 (MH⁻, 100%).

Example 1.9

Preparation of N-({[Bis-(4-chloro-phenyl)-methyl]-carbamoyl}-methyl)-3-phenyl-propionamide

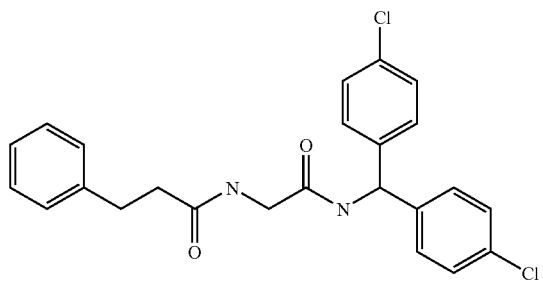

Prepared in analogy to example 1.1 from C,C-bis-(4-chloro-phenyl)-methylamine (CA [14212-38-5]) and (3-phenyl-propionylamino)-acetic acid (CA [56613-60-6]).

MS (m/e): 439.2 (MH⁻, 100%).

Example 1.10

Preparation of rac-2-(3-Benzyl-ureido)-N-[(4-chloro-phenyl)-phenyl-methyl]-acetamide

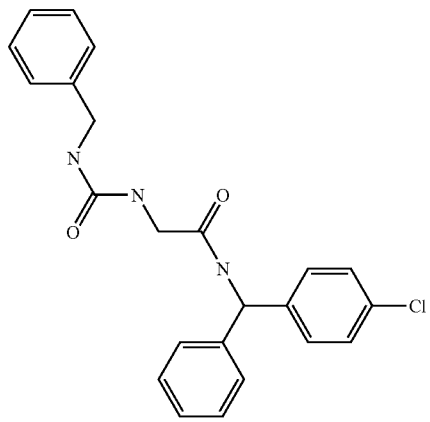

A solution of 0.2 mmol rac-2-amino-N-[(4-chloro-phenyl)-phenyl-methyl]-acetamide hydrochloride (Example 3.1) and 0.28 mmol of DIPEA in 2 ml of dioxane was treated with 0.2 mmol of benzylisocyanate. The mixture was stirred at room temperature for 48 hours, concentrated and diluted with diethyl ether. The solid was filtered off, dissolved in dichloromethane and extracted 2 times with a diluted solution of citric acid. The organic phase was dried and concentrated. The residue was triturated with diethyl ether to give the title compound as a colorless solid. Yield=93%.

MS (m/e): 406.4 (MH⁻, 100%).

Example 1.11

Preparation of rac-3-Phenyl-N-({[phenyl-(4-trifluoromethyl-phenyl)-methyl]-carbamoyl}-methyl)-propionamide

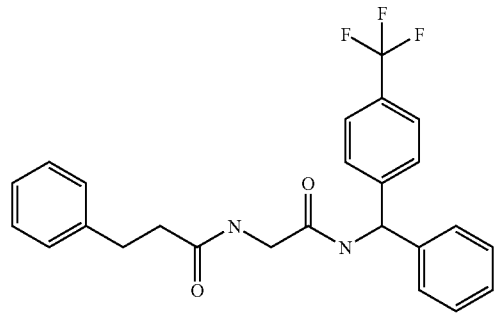

Prepared in analogy to example 1.1 from rac-C-phenyl-C-(4-trifluoromethyl-phenyl)-methylamine (CA [154238-38-2]) and (3-phenyl-propionylamino)-acetic acid (CA [56613-60-6]).

MS (m/e): 439.2 (MH⁻, 100%).

Example 1.12

Preparation of rac-N-({[(4-Chloro-phenyl)-phenyl-methyl]-carbamoyl}-methyl)-4-phenyl-butyramide

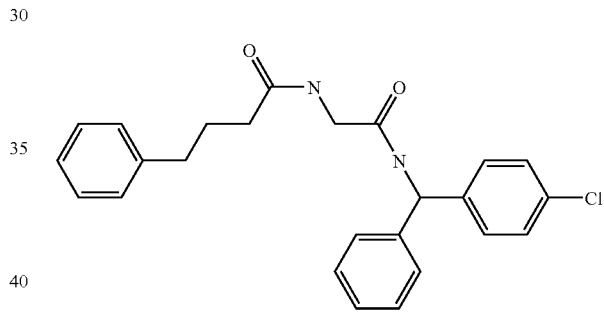

A suspension of 0.32 mmol rac-2-amino-N-[(4-chlorophenyl)-phenyl-methyl]-acetamide hydrochloride (Example 3.1) in 5 ml acetonitrile was treated successively with 0.32 mmol 4-phenylbutyric acid, 1.61 mmol DIPEA and 0.35 mmol TBTU. The reaction mixture was stirred for 1 hour at room temperature and concentrated. Chromatography (SiO₂; dichloromethane/methanol) gave the title compound as a colorless solid. Yield=71%. MS (m/e): 419.3 (MH⁻, 100%).

Example 1.13

Preparation of rac-3-Chloro-N-({[(4-chloro-phenyl)-phenyl-methyl]-carbamoyl}-methyl)-benzamide

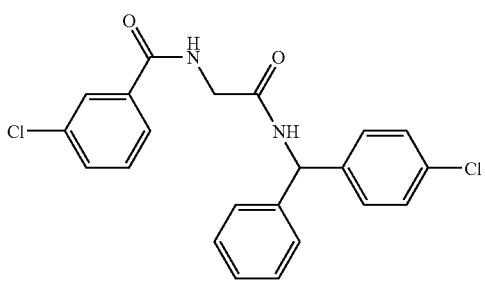

A suspension of 0.32 mmol rac-2-amino-N-[(4-chlorophenyl)-phenyl-methyl]-acetamide hydrochloride (Example 3.1) in 5 ml of dichloromethane was treated with 1.61 mmol of triethylamine. The resulting slurry was cooled to 0° C. and 0.35 mmol of 3-chlorobenzoyl chloride was added. The mixture was stirred for 1 hour at room temperature, concentrated and hydrolysed. The organic phase was dried over magnesium sulfate and concentrated. The residue was triturated with diethyl ether to give the title compound as a colorless solid. Yield=97%.

MS (m/e): 411.1 (MH⁻, 100%).

Example 1.14

Preparation of rac-4-Chloro-N-({[(4-chloro-phenyl)-phenyl-methyl]-carbamoyl}-methyl)-benzamide

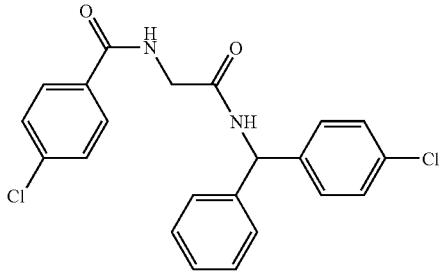

Prepared in analogy to example 1.13 from rac-2-amino-N-[(4-chloro-phenyl)-phenyl-methyl]-acetamide hydrochloride (Example 3.1) and 4-chlorobenzoyl chloride.

MS (m/e): 411.0 (MH⁻, 100%).

Example 1.15

Preparation of rac-N-({[(4-Chloro-phenyl)-phenyl-methyl]-carbamoyl}-methyl)-4-methoxy-benzamide

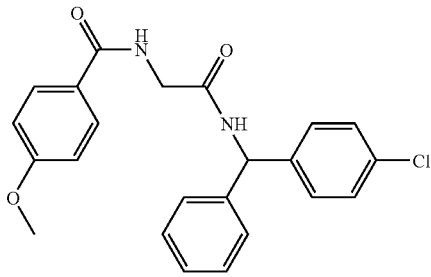

Prepared in analogy to example 1.13 from rac-2-amino-N-[(4-chloro-phenyl)-phenyl-methyl]-acetamide hydrochloride (Example 3.1) and 4-methoxybenzoyl chloride.

MS (m/e): 407.4 (MH⁻, 100%).

Example 1.16

Preparation of rac-3-Phenyl-N-{[(phenyl-p-tolyl-methyl)-carbamoyl]-methyl}-propionamide

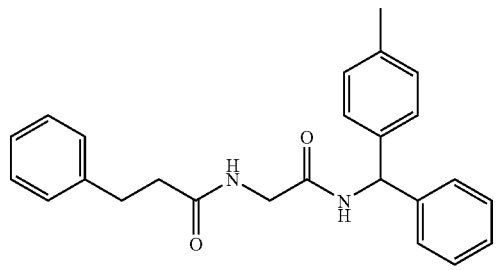

Prepared in analogy to example 1.1 from (3-phenyl-propionylamino)-acetic acid (CA [56613-60-6]) and rac-C-phenyl-C-p-tolyl-methylamine (CA [55095-21-1]).

MS (m/e): 385.2 (MH⁻, 100%).

Example 1.17

Preparation of rac-N-({[(2-Chloro-5-trifluoromethyl-phenyl)-phenyl-methyl]-carbamoyl}-methyl)-3-phenyl-propionamide

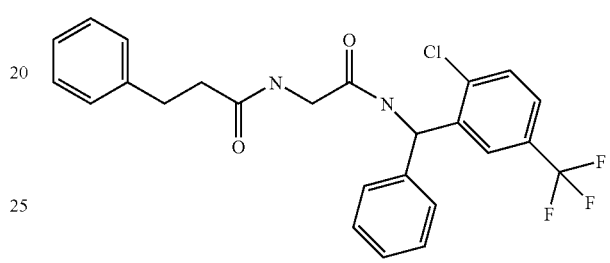

Prepared in analogy to example 1.1 from (3-phenyl-propionylamino)-acetic acid (CA [56613-60-6]) and rac-C-(2-Chloro-5-trifluoromethyl-phenyl)-C-phenyl-methylamine hydrochloride (CA [13954-13-7]).

MS (m/e): 473.1 (MH⁻, 100%).

Example 1.18

Preparation of (−)-4-Chloro-N-({[(R)-(4-chloro-phenyl)-phenyl-methyl]-carbamoyl}-methyl)-benzamide

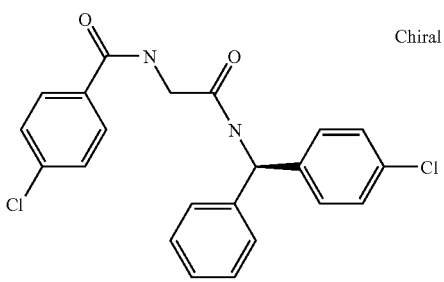

This compound was obtained by separation of the enantiomers from example 1.14 using preparative HPLC (column=Chiralcel OD; solvent=heptane/ethanol 85:15). Specific rotation: −19.4° (c=1; methanol).

Example 1.19

Preparation of (+)-4-Chloro-N-({[(R)-(4-chloro-phenyl)-phenyl-methyl]-carbamoyl}-methyl)-benzamide

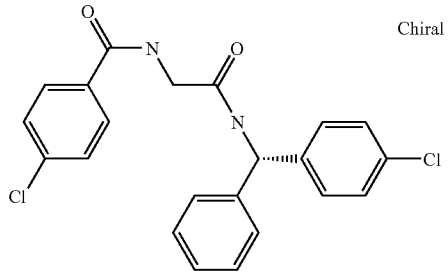

This compound was obtained by separation of the enantiomers from example 1.14 using preparative HPLC (column=Chiralcel OD; solvent=heptane/ethanol 85:15). Specific rotation: +17.6° (c=1; methanol).

Example 1.20

Preparation of rac-N-({[(4-Chloro-phenyl)-phenyl-methyl]-carbamoyl}-methyl)-4-trifluoromethyl-benzamide

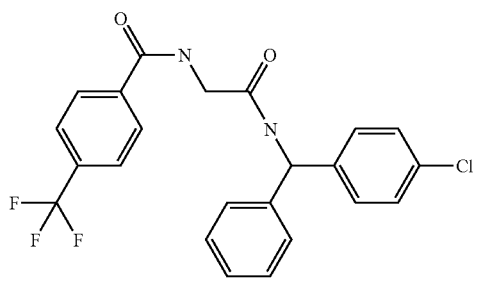

Prepared in analogy to example 1.12 from rac-2-amino-N-[(4-chloro-phenyl)-phenyl-methyl]-acetamide hydrochloride (Example 3.1) and 4-(trifluoromethyl)benzoic acid.
MS (m/e): 445.1 (MH$^-$, 100%).

Example 1.21

Preparation of rac-N-({[(4-Chloro-phenyl)-phenyl-methyl]-carbamoyl}-methyl)-4-isopropyl-benzamide

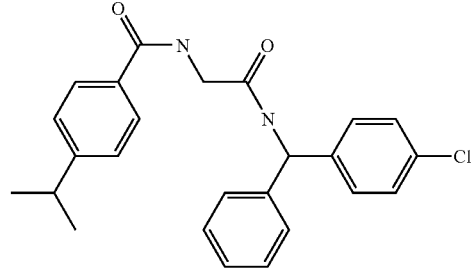

Prepared in analogy to example 1.12 from rac-2-amino-N-[(4-chloro-phenyl)-phenyl-methyl]-acetamide hydrochloride (Example 3.1) and 4-isopropylbenzoic acid.
MS (m/e): 419.3 (MH$^-$, 100%).

Example 1.22

Preparation of rac-4-Acetyl-N-({[(4-chloro-phenyl)-phenyl-methyl]-carbamoyl}-methyl)-benzamide

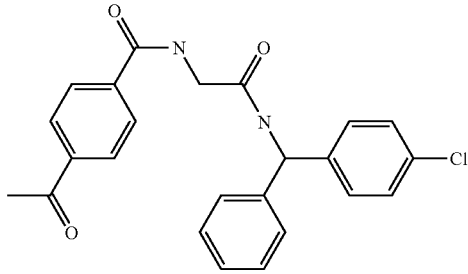

Prepared in analogy to example 1.12 from rac-2-amino-N-[(4-chloro-phenyl)-phenyl-methyl]-acetamide hydrochloride (Example 3.1) and 4-acetylbenzoic acid.
MS (m/e): 419.3 (MH$^-$, 100%).

Example 1.23

Preparation of rac-3-Phenyl-N-({[phenyl-(3-trifluoromethyl-phenyl)-methyl]-carbamoyl}-methyl)-propionamide

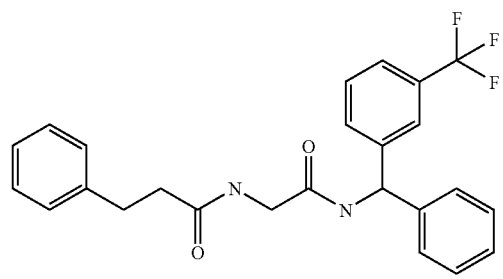

Prepared in analogy to example 1.1 from (3-phenyl-propionylamino)-acetic acid (CA [56613-60-6]) and rac-C-phenyl-C-(3-trifluoromethyl-phenyl)-methylamine (CA [70428-92-1]).
MS (m/e): 441.5 (M+H, 80%).

Example 1.24

Preparation of rac-N-({[(4-Chloro-phenyl)-phenyl-methyl]-carbamoyl}-methyl)-4-methanesulfonyl-benzamide

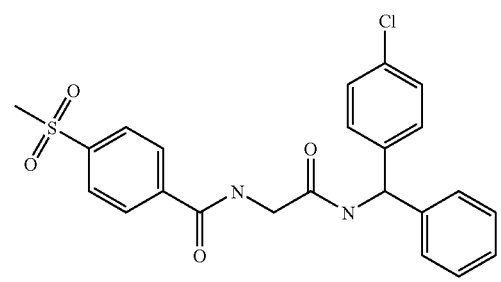

Prepared in analogy to example 1.12 from rac-2-amino-N-[(4-chloro-phenyl)-phenyl-methyl]-acetamide hydrochloride (Example 3.1) and 4-methylsulphonylbenzoic acid.
MS (m/e): 455.2 (MH⁻, 100%).

Example 1.25

Preparation of rac-N-({[(4-Chloro-phenyl)-phenyl-methyl]-carbamoyl}-methyl)-4-nitro-benzamide

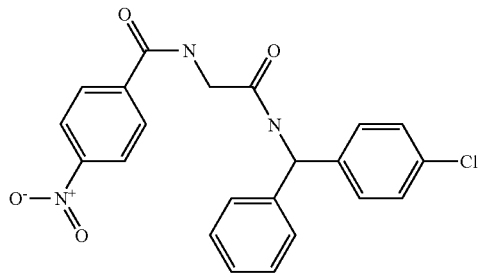

Prepared in analogy to example 1.12 from rac-2-amino-N-[(4-chloro-phenyl)-phenyl-methyl]-acetamide hydrochloride (Example 3.1) and 4-nitrobenzoic acid.
MS (m/e): 422.1 (MH⁻, 100%).

Example 1.26

Preparation of rac-N-({[(4-Chloro-phenyl)-phenyl-methyl]-carbamoyl}-methyl)-4-cyano-benzamide

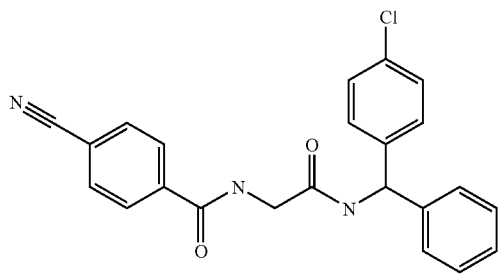

Prepared in analogy to example 1.12 from rac-2-amino-N-[(4-chloro-phenyl)-phenyl-methyl]-acetamide hydrochloride (Example 3.1) and 4-cyanobenzoic acid.
MS (m/e): 402.3 (MH⁻, 100%).

Example 1.27

Preparation of rac-3-Phenyl-N-({[phenyl-(2-trifluoromethyl-phenyl)-methyl]-carbamoyl}-methyl)-propionamide

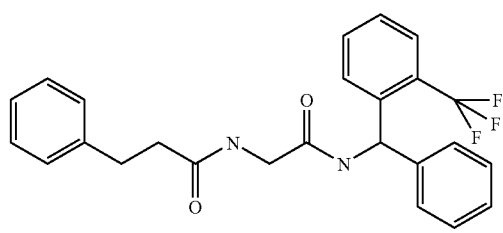

Prepared in analogy to example 1.1 from mmol (3-phenyl-propionylamino)-acetic acid (CA [56613-60-6]) and rac-C-phenyl-C-(2-trifluoromethyl-phenyl)-methylamine hydrochloride (CA [49703-62-0]).
MS (m/e): 441.5 (M+H⁺).

Example 1.28

Preparation of rac-N-({[(4-Chloro-phenyl)-phenyl-methyl]-carbamoyl}-methyl)-isonicotinamide

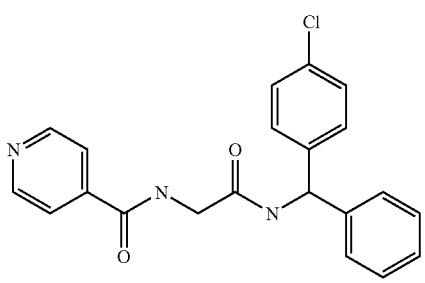

Prepared in analogy to example 1.12 from rac-2-amino-N-[(4-chloro-phenyl)-phenyl-methyl]-acetamide hydrochloride (Example 3.1) and isonicotinic acid.
MS (m/e): 378.3 (MH⁻, 100%).

Example 1.29

Preparation of rac-N-({[(4-Chloro-phenyl)-phenyl-methyl]-carbamoyl}-methyl)-4-fluoro-benzamide

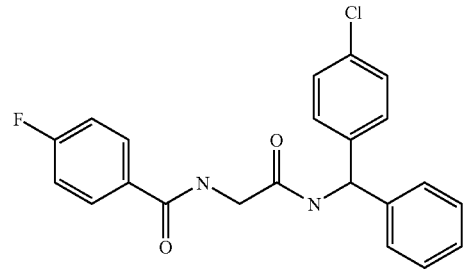

Prepared in analogy to example 1.12 from rac-2-amino-N-[(4-chloro-phenyl)-phenyl-methyl]-acetamide hydrochloride (Example 3.1) and 4-fluorobenzoic acid.
MS (m/e): 395.1 (MH⁻, 100%).

Example 1.30

Preparation of rac-N-({[Phenyl-(3-trifluoromethyl-phenyl)-methyl]-carbamoyl}-methyl)-benzamide

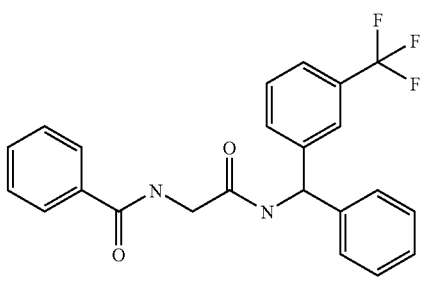

Prepared in analogy to example 1.1 from rac-C-phenyl-C-(3-trifluoromethyl-phenyl)-methylamine (CA [70428-92-1]) and hippuric acid.
MS (m/e): 411.2 (MH⁻, 100%).

Example 1.31

Preparation of N-({[Bis-(4-trifluoromethyl-phenyl)-methyl]-carbamoyl}-methyl)-benzamide

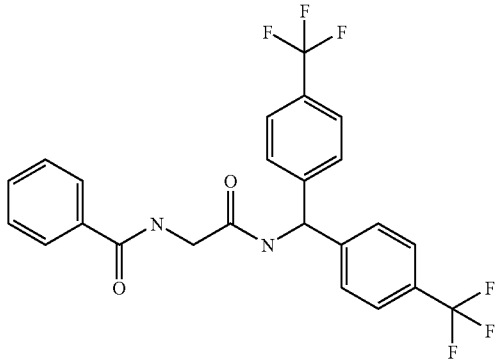

Prepared in analogy to example 1.1 from C,C-bis-(4-trifluoromethyl-phenyl)-methylamine (example 4.1) and hippuric acid.
MS (m/e): 481.4 (M+H, 100%).

Example 1.32

Preparation of rac-5-Nitro-thiophene-2-carboxylic acid ({[(4-chloro-phenyl)-phenyl-methyl]-carbamoyl}-methyl)-amide

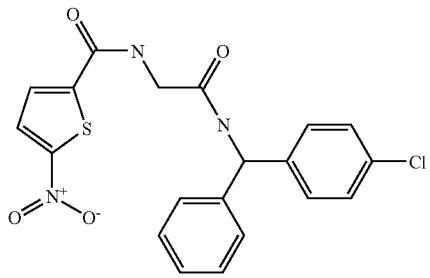

Prepared in analogy to example 1.12 from rac-2-amino-N-[(4-chloro-phenyl)-phenyl-methyl]-acetamide hydrochloride (Example 3.1) and 5-nitrothiophene-2-carboxylic acid.
MS (m/e): 428.3 (MH⁻, 100%).

Example 1.33

Preparation of rac-Thiophene-2-carboxylic acid ({[(4-chloro-phenyl)-phenyl-methyl]-carbamoyl}-methyl)-amide

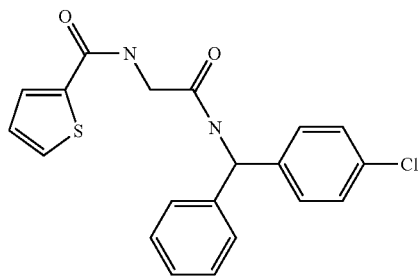

Prepared in analogy to example 1.12 from rac-2-amino-N-[(4-chloro-phenyl)-phenyl-methyl]-acetamide hydrochloride (Example 3.1) and 2-thiophenecarboxylic acid.
MS (m/e): 383.1 (MH⁻, 100%).

Example 1.34

Preparation of rac-Thiophene-3-carboxylic acid ({[(4-chloro-phenyl)-phenyl-methyl]-carbamoyl}-methyl)-amide

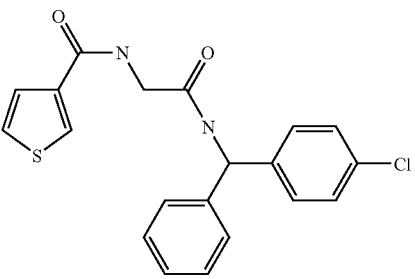

Prepared in analogy to example 1.12 from rac-2-amino-N-[(4-chloro-phenyl)-phenyl-methyl]-acetamide hydrochloride (Example 3.1) and 3-thiophenecarboxylic acid.
MS (m/e): 383.1 (MH⁻, 100%).

Example 1.35

Preparation of rac-N-({[(4-Chloro-phenyl)-phenyl-methyl]-carbamoyl}-methyl)-4-methyl-benzamide

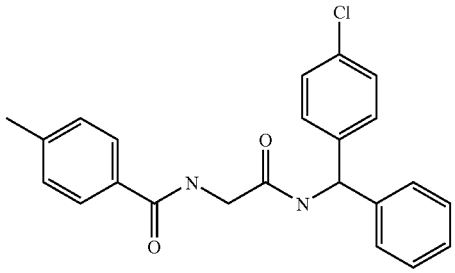

Prepared in analogy to example 1.12 from rac-2-amino-N-[(4-chloro-phenyl)-phenyl-methyl]-acetamide hydrochloride (Example 3.1) and p-toluic acid.
MS (m/e): 391.2 (MH⁻, 100%).

Example 1.36

Preparation of rac-Isoxazole-5-carboxylic acid ({[(4-chloro-phenyl)-phenyl-methyl]-carbamoyl}-methyl)-amide

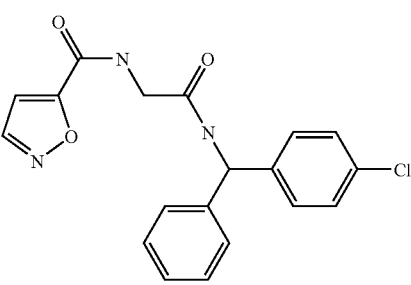

Prepared in analogy to example 1.12 from rac-2-amino-N-[(4-chloro-phenyl)-phenyl-methyl]-acetamide hydrochloride (Example 3.1) and isoxazole-5-carboxylic acid.
MS (m/e): 368.1 (MH−, 100%).

Example 1.37

Preparation of rac-5-Methyl-isoxazole-3-carboxylic acid ({[(4-chloro-phenyl)-phenyl-methyl]-carbamoyl}-methyl)-amide

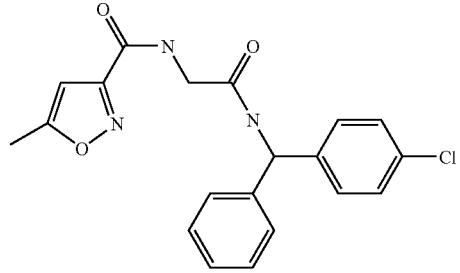

Prepared in analogy to example 1.12 from rac-2-amino-N-[(4-chloro-phenyl)-phenyl-methyl]-acetamide hydrochloride (Example 3.1) and 5-methylisoxazole-3-carboxylic acid.
MS (m/e): 382.0 (MH−, 100%).

Example 1.38

Preparation of rac-4-Chloro-N-({[phenyl-(4-trifluoromethyl-phenyl)-methyl]-carbamoyl}-methyl)-benzamide

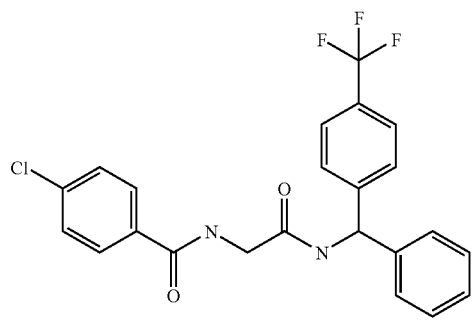

Prepared in analogy to example 1.12 from rac-2-amino-N-[phenyl-(4-trifluoromethyl-phenyl)-methyl]-acetamide hydrochloride (example 3.2) and 4-chlorobenzoic acid.
MS (m/e): 445.1 (MH−, 100%).

Example 1.39

Preparation of rac-N-({[(2,4-Dichloro-phenyl)-phenyl-methyl]-carbamoyl}-methyl)-benzamide

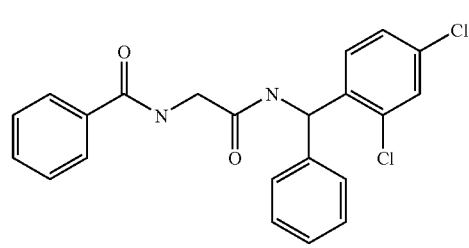

Prepared in analogy to example 1.1 from rac-C-(2,4-dichloro-phenyl)-C-phenyl-methylamine (example 4.2) and hippuric acid.
MS (m/e): 411.1 (M+H, 100%).

Example 1.40

Preparation of rac-5-Chloro-thiophene-2-carboxylic acid ({[(4-chloro-phenyl)-phenyl-methyl]-carbamoyl}-methyl)-amide

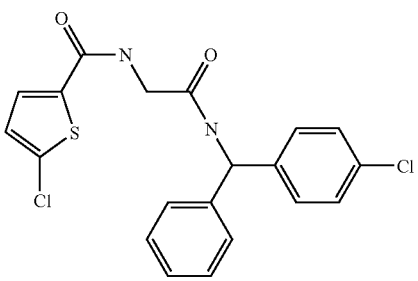

Prepared in analogy to example 1.12 from rac-2-amino-N-[(4-chloro-phenyl)-phenyl-methyl]-acetamide hydrochloride (Example 3.1) and 5-chloro-2-thiophenecarboxylic acid.
MS (m/e): 417.1 (MH−, 100%).

Example 1.41

Preparation of rac-4-Fluoro-N-{[(phenyl-p-tolyl-methyl)-carbamoyl]-methyl}-benzamide

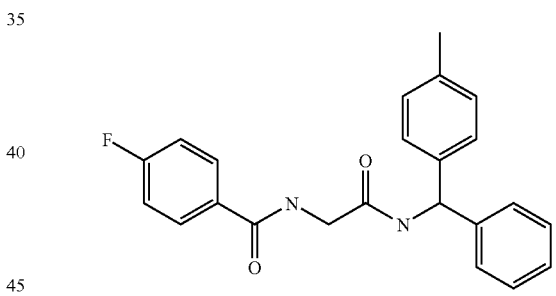

Prepared in analogy to example 1.12 from rac-2-amino-N-(phenyl-p-tolyl-methyl)-acetamide (Example 3.3) and 4-fluorobenzoic acid.
MS (m/e): 375.3 (M+H, 100%).

Example 1.42

Preparation of rac-4-Chloro-N-{[(phenyl-p-tolyl-methyl)-carbamoyl]-methyl}-benzamide

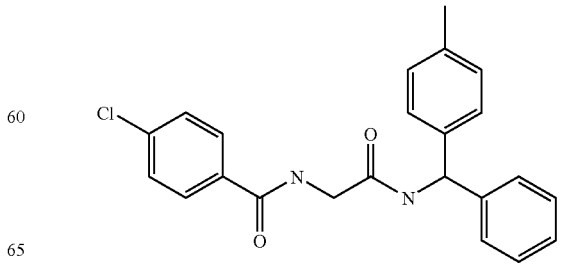

Prepared in analogy to example 1.12 from rac-2-amino-N-(phenyl-p-tolyl-methyl)-acetamide (Example 3.3) and 4-chlorobenzoic acid.
MS (m/e): 391.2 (MH⁻, 53%).

Example 1.43

Preparation of rac-4-Fluoro-N-({[phenyl-(3-trifluoromethyl-phenyl)-methyl]-carbamoyl}-methyl)-benzamide

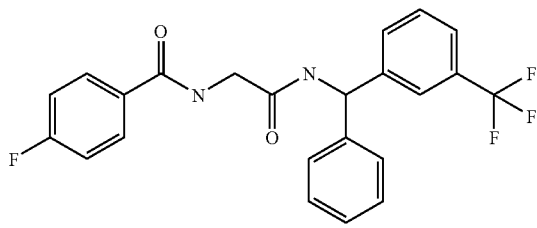

Prepared in analogy to example 1.1 from (4-fluoro-benzoylamino)-acetic acid (CA [366-79-0]) and rac-C-phenyl-C-(3-trifluoromethyl-phenyl)-methylamine (CA [70428-92-1]). MS (m/e): 429.4 (MH⁻, 100%).

Example 1.44

Preparation of rac-4-Cyano-N-({[phenyl-(3-trifluoromethyl-phenyl)-methyl]-carbamoyl}-methyl)-benzamide

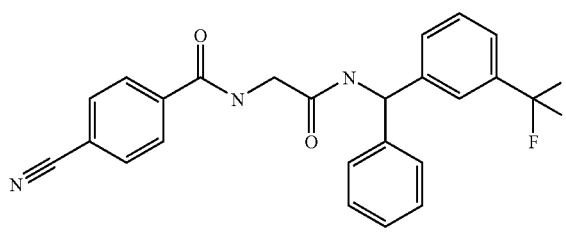

Prepared in analogy to example 1.1 from (4-cyano-benzoylamino)-acetic acid (CA [90290-83-8]) and rac-C-phenyl-C-(3-trifluoromethyl-phenyl)-methylamine (CA [70428-92-1]). MS (m/e): 436.1 (MH⁻, 100%).

Example 1.45

Preparation of rac-N-({[(4-Chloro-phenyl)-phenyl-methyl]-carbamoyl}-methyl)-3-fluoro-benzamide

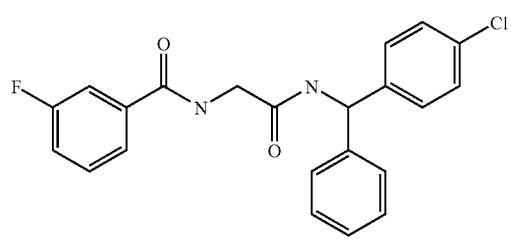

Prepared in analogy to example 1.12 from rac-2-amino-N-[(4-chloro-phenyl)-phenyl-methyl]-acetamide hydrochloride (Example 3.1) and 3-fluorobenzoic acid.
MS (m/e): 398.2 (7%) & 396.2 (22%), (M+H).

Example 1.46

Preparation of rac-N-({[(4-Chloro-phenyl)-phenyl-methyl]-carbamoyl}-methyl)-2-trifluoromethyl-benzamide

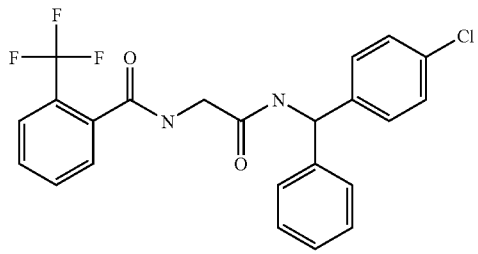

Prepared in analogy to example 1.12 from rac-2-amino-N-[(4-chloro-phenyl)-phenyl-methyl]-acetamide hydrochloride (Example 3.1) and 2-trifluoromethylbenzoic acid.
MS (m/e): 448.2 (6%) & 446.1 (24%), (M+H).

Example 1.47

Preparation of N-[(Benzhydryl-carbamoyl)-methyl]-4-fluoro-benzamide

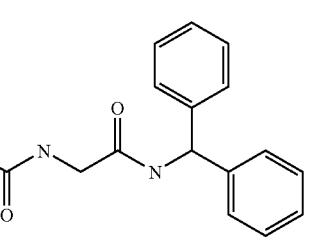

Prepared in analogy to example 1.1 from p-fluoro-hippuric acid (CA [366-79-0]) and C,C-diphenylmethylamine.
MS (m/e): 363.3 (M+H).

Example 1.48

Preparation of rac-N-({[(4-Chloro-phenyl)-phenyl-methyl]-carbamoyl}-methyl)-4-methoxy-3-methyl-benzamide

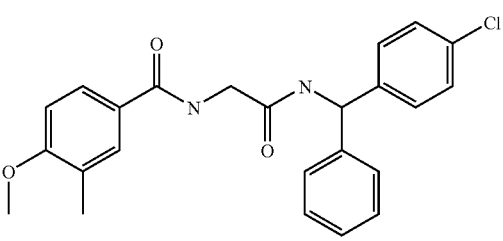

Prepared in analogy to example 1.12 from rac-2-amino-N-[(4-chloro-phenyl)-phenyl-methyl]-acetamide hydrochloride (Example 3.1) and 4-methoxy-3-methylbenzoic acid. MS (m/e): 420.8 (MH⁻, 100%).

Example 1.49

Preparation of rac-N-({[(4-Chloro-phenyl)-phenyl-methyl]-carbamoyl}-methyl)-3-fluoro-4-methoxy-benzamide

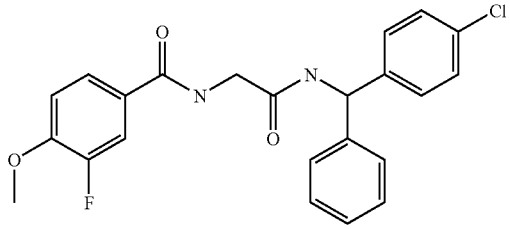

Prepared in analogy to example 1.12 from rac-2-amino-N-[(4-chloro-phenyl)-phenyl-methyl]-acetamide hydrochloride (Example 3.1) and 3-fluoro-4-methoxybenzoic acid. MS (m/e): 424.9 (MH⁻, 100%).

Example 1.50

Preparation of rac-N-({[(4-Chloro-phenyl)-phenyl-methyl]-carbamoyl}-methyl)-3,4-difluoro-benzamide

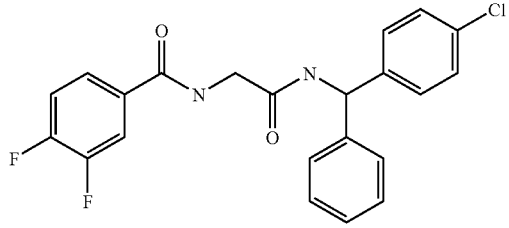

Prepared in analogy to example 1.12 from rac-2-amino-N-[(4-chloro-phenyl)-phenyl-methyl]-acetamide hydrochloride (Example 3.1) and 3,4-difluorobenzoic acid. MS (m/e): 412.9 (MH⁻, 100%).

Example 1.51

Preparation of rac-N-({[(4-Chloro-phenyl)-phenyl-methyl]-carbamoyl}-methyl)-4-fluoro-3-methyl-benzamide

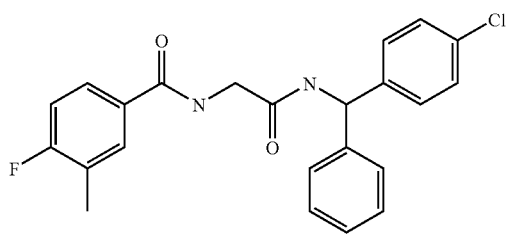

Prepared in analogy to example 1.12 from rac-2-amino-N-[(4-chloro-phenyl)-phenyl-methyl]-acetamide hydrochloride (Example 3.1) and 4-fluoro-3-methylbenzoic acid. MS (m/e): 409.0 (MH⁻, 100%).

Example 1.52

Preparation of rac-N-({[(4-Chloro-phenyl)-phenyl-methyl]-carbamoyl}-methyl)-3,5-difluoro-benzamide

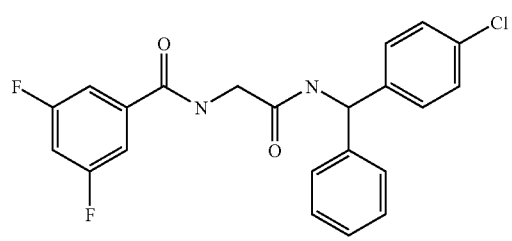

Prepared in analogy to example 1.12 from rac-2-amino-N-[(4-chloro-phenyl)-phenyl-methyl]-acetamide hydrochloride (Example 3.1) and 3,5-difluorobenzoic acid. MS (m/e): 412.9 (MH⁻, 100%).

Example 1.53

Preparation of rac-4-Chloro-N-({[(4-chloro-phenyl)-phenyl-methyl]-carbamoyl}-methyl)-3-methyl-benzamide

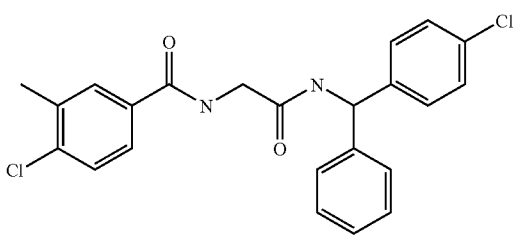

Prepared in analogy to example 1.12 from rac-2-amino-N-[(4-chloro-phenyl)-phenyl-methyl]-acetamide hydrochloride (Example 3.1) and 4-chloro-3-methylbenzoic acid. MS (m/e): 425.0 (MH⁻, 100%).

Example 1.54

Preparation of rac-N-({[(4-Chloro-phenyl)-phenyl-methyl]-carbamoyl}-methyl)-4-methoxy-2-methyl-benzamide

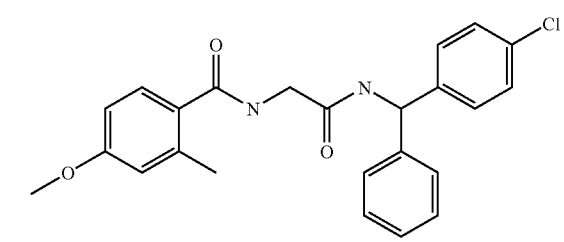

Prepared in analogy to example 1.12 from rac-2-amino-N-[(4-chloro-phenyl)-phenyl-methyl]-acetamide hydrochloride (Example 3.1) and 4-methoxy-2-methylbenzoic acid. MS (m/e): 421.0 (MH⁻, 100%).

Example 1.55

Preparation of rac-N-({[(4-Chloro-phenyl)-phenyl-methyl]-carbamoyl}-methyl)-4-difluoromethoxy-benzamide

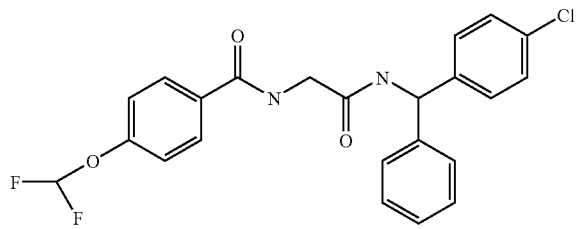

Prepared in analogy to example 1.12 from rac-2-amino-N-[(4-chloro-phenyl)-phenyl-methyl]-acetamide hydrochloride (Example 3.1) and 4-difluoromethoxybenzoic acid.
MS (m/e): 443.2 (MH⁻, 100%).

Example 1.56

Preparation of rac-N-({[(4-Chloro-phenyl)-phenyl-methyl]-carbamoyl}-methyl)-4-methoxy-3,5-dimethyl-benzamide

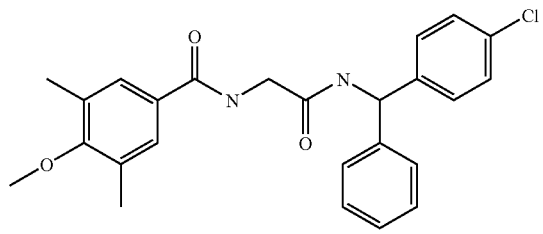

Prepared in analogy to example 1.12 from rac-2-amino-N-[(4-chloro-phenyl)-phenyl-methyl]-acetamide hydrochloride (Example 3.1) and 3,5-dimethyl-4-methoxybenzoic acid.
MS (m/e): 435.2 (MH⁻, 100%).

Example 1.57

Preparation of rac-N-({[(4-Chloro-phenyl)-phenyl-methyl]-carbamoyl}-methyl)-4-trifluoromethoxy-benzamide

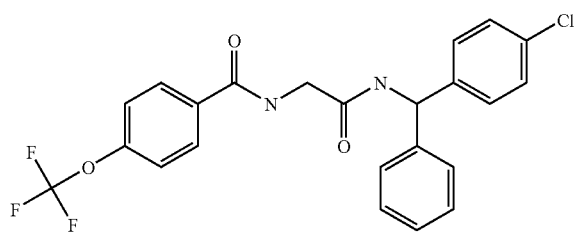

Prepared in analogy to example 1.12 from rac-2-amino-N-[(4-chloro-phenyl)-phenyl-methyl]-acetamide hydrochloride (Example 3.1) and 4-(trifluoromethoxy)benzoic acid.
MS (m/e): 461.1 (MH⁻, 100%).

Example 1.58

Preparation of rac-2,3-Dihydro-benzofuran-5-carboxylic acid ({[(4-chloro-phenyl)-phenyl-methyl]-carbamoyl}-methyl)-amide

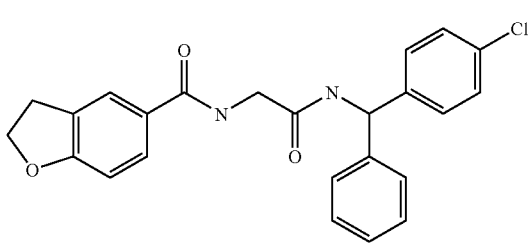

Prepared in analogy to example 1.12 from rac-2-amino-N-[(4-chloro-phenyl)-phenyl-methyl]-acetamide hydrochloride (Example 3.1) and 2,3-dihydrobenzo(B)furan-5-carboxylic acid.
MS (m/e): 419.1 (MH⁻, 100%).

Example 1.59

Preparation of rac-4-Chloro-N-({[(4-chloro-phenyl)-phenyl-methyl]-carbamoyl}-methyl)-2-nitro-benzamide

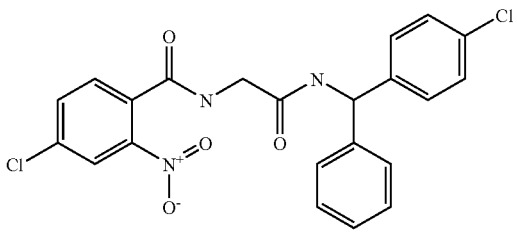

Prepared in analogy to example 1.12 from rac-2-amino-N-[(4-chloro-phenyl)-phenyl-methyl]-acetamide hydrochloride (Example 3.1) and 4-chloro-2-nitrobenzoic acid.
MS (m/e): 456.2 (MH⁻, 100%).

Example 1.60

Preparation of rac-Quinoxaline-6-carboxylic acid ({[(4-chloro-phenyl)-phenyl-methyl]-carbamoyl}-methyl)-amide

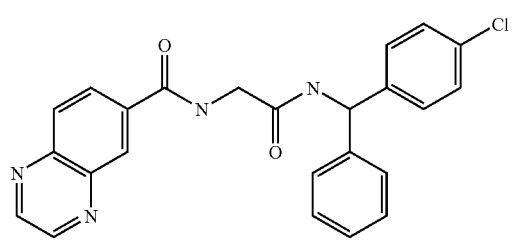

Prepared in analogy to example 1.12 from rac-2-amino-N-[(4-chloro-phenyl)-phenyl-methyl]-acetamide hydrochloride (Example 3.1) and quinoxaline-6-carboxylic acid.
MS (m/e): 429.2 (MH⁻, 100%).

Example 1.61

Preparation of rac-N-({[(4-Chloro-phenyl)-phenyl-methyl]-carbamoyl}-methyl)-2,4-difluoro-benzamide

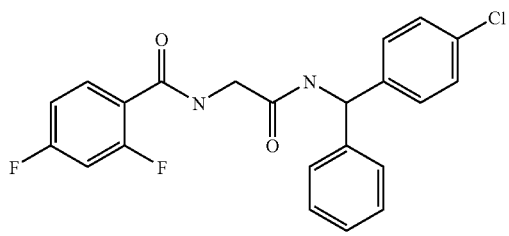

Prepared in analogy to example 1.12 from rac-2-amino-N-[(4-chloro-phenyl)-phenyl-methyl]-acetamide hydrochloride (Example 3.1) and 2,4-difluorobenzoic acid.
MS (m/e): 413.1 (MH⁻, 100%).

Example 1.62

Preparation of rac-N-({[(4-Chloro-phenyl)-phenyl-methyl]-carbamoyl}-methyl)-2,4,5-trifluoro-benzamide

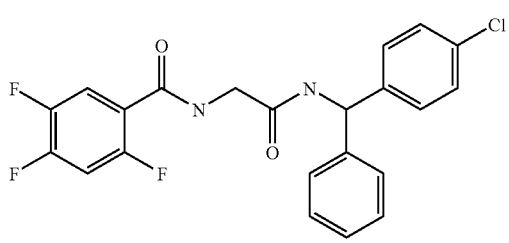

Prepared in analogy to example 1.12 from rac-2-amino-N-[(4-chloro-phenyl)-phenyl-methyl]-acetamide hydrochloride (Example 3.1) and 2,4,5-trifluorobenzoic acid.
MS (m/e): 431.2 (MH⁻, 100%).

Example 1.63

Preparation of rac-N-({[(3-Chloro-phenyl)-phenyl-methyl]-carbamoyl}-methyl)-4-fluoro-benzamide

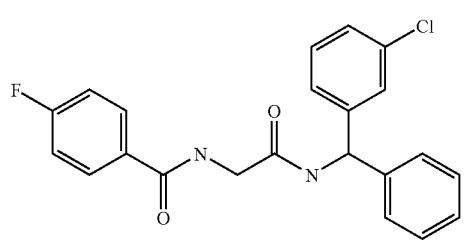

Prepared in analogy to example 1.1 from 4-fluoro-hippuric acid (CA [366-79-0]) and rac-C-(3-chloro-phenyl)-C-phenyl-methylamine (CA [55095-14-2]).
MS (m/e): 397.3 (M+H, 100%).

Example 1.64

Preparation of rac-2,4-Dichloro-N-({[(4-chloro-phenyl)-phenyl-methyl]-carbamoyl}-methyl)-benzamide

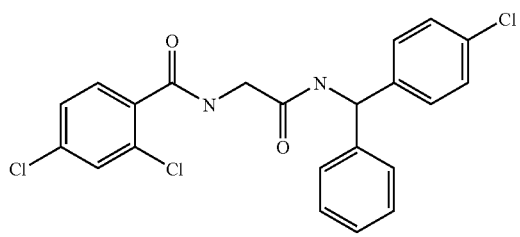

Prepared in analogy to example 1.12 from rac-2-amino-N-[(4-chloro-phenyl)-phenyl-methyl]-acetamide hydrochloride (Example 3.1) and 2,4-dichlorobenzoic acid.
MS (m/e): 445.1 (MH⁻, 100%).

Example 1.65

Preparation of rac-2-Chloro-N-({[(4-chloro-phenyl)-phenyl-methyl]-carbamoyl}-methyl)-4-fluoro-benzamide

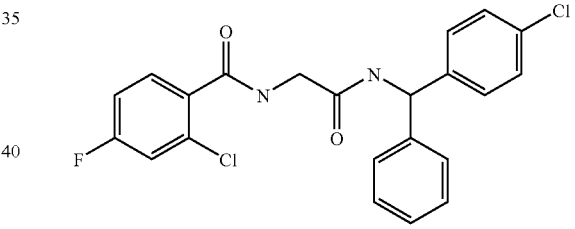

Prepared in analogy to example 1.12 from rac-2-amino-N-[(4-chloro-phenyl)-phenyl-methyl]-acetamide hydrochloride (Example 3.1) and 2-chloro-4-fluorobenzoic acid.
MS (m/e): 429.2 (MH⁻, 100%).

Example 1.66

Preparation of rac-4-Chloro-N-({[(4-chloro-phenyl)-phenyl-methyl]-carbamoyl}-methyl)-2-methyl-benzamide

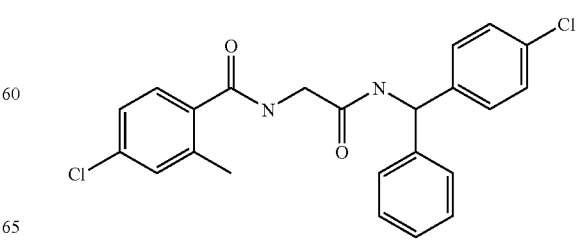

Prepared in analogy to example 1.12 from rac-2-amino-N-[(4-chloro-phenyl)-phenyl-methyl]-acetamide hydrochloride (Example 3.1) and 4-chloro-2-methylbenzoic acid.
MS (m/e): 425.1 (MH⁻, 100%).

Example 1.67

Preparation of rac-4-Fluoro-N-{[(phenyl-m-tolyl-methyl)-carbamoyl]-methyl}-benzamide

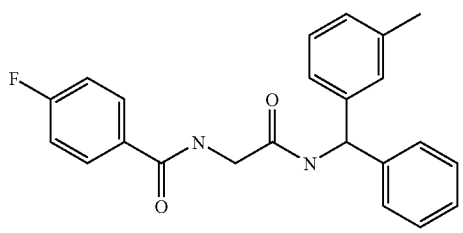

Prepared in analogy to example 1.1 from 4-fluoro-hippuric acid (CA [366-79-0]) and rac-C-phenyl-C-m-tolyl-methylamine (CA [55095-20-0]).
MS (m/e): 377.4 (M+H, 19%).

Example 1.68

Preparation of rac-4-Fluoro-N—((S)-1-{[phenyl-(3-trifluoromethyl-phenyl)-methyl]-carbamoyl}-ethyl)-benzamide

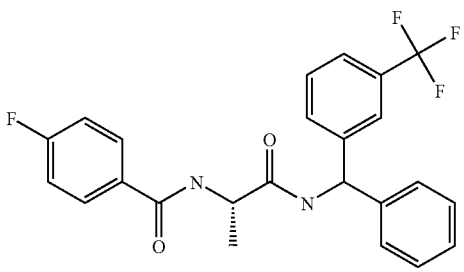

Prepared in analogy to example 1.1 from (S)-2-(4-fluoro-benzoylamino)-propionic acid (CA [214629-12-6]) and rac-C-phenyl-C-(3-trifluoromethyl-phenyl)-methylamine (CA [70428-92-1]).
MS (m/e): 445.4 (M+H, 71%).

Example 1.69

Preparation of rac-4-Fluoro-N-({[(4-fluoro-phenyl)-phenyl-methyl]-carbamoyl}-methyl)-benzamide

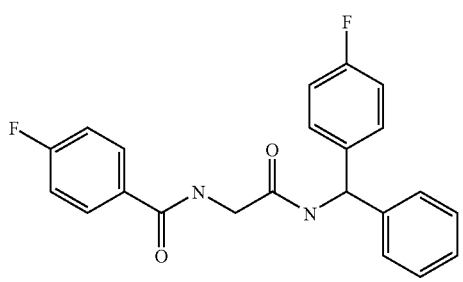

Prepared in analogy to example 1.1 from 4-fluoro-hippuric acid (CA [366-79-0]) and rac-C-(4-fluoro-phenyl)-C-phenyl-methylamine (CA [55095-26-6]).
MS (m/e): 381.3 (M+H, 10%).

Example 1.70

Preparation of N-({[Bis-(3-fluoro-phenyl)-methyl]-carbamoyl}-methyl)-4-fluoro-benzamide

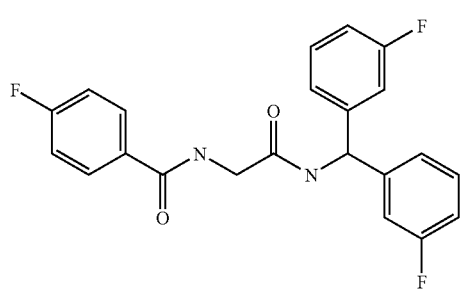

Prepared in analogy to example 1.1 from 4-fluoro-hippuric acid (CA [366-79-0]) and C,C-bis-(3-fluoro-phenyl)-methylamine (CA [261925-16-0]).
MS (m/e): 399.1 (M+H).

Example 1.71

Preparation of rac-4-Fluoro-N-({[(4-methoxy-phenyl)-phenyl-methyl]-carbamoyl}-methyl)-benzamide

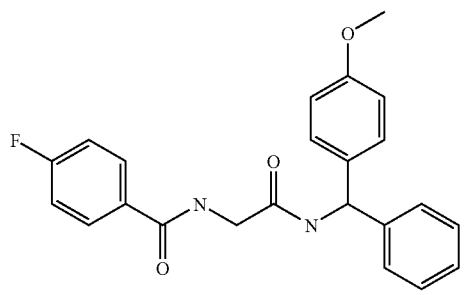

Prepared in analogy to example 1.1 from 4-fluoro-hippuric acid (CA [366-79-0]) and rac-C-(4-methoxy-phenyl)-C-phenyl-methylamine (CA [2538-34-3]).
MS (m/e): 392.9 (M+H).

Example 1.72

Preparation of rac-N-({[(3,5-Difluoro-phenyl)-phenyl-methyl]-carbamoyl}-methyl)-4-fluoro-benzamide

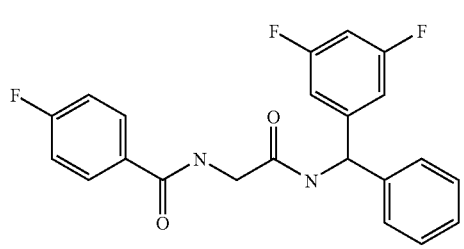

Prepared in analogy to example 1.1 from 4-fluoro-hippuric acid (CA [366-79-0]) and rac-C-(3,5-difluoro-phenyl)-C-phenyl-methylamine (example 4.3).
MS (m/e): 399.3 (M+H).

Example 1.73

Preparation of rac-N-({[(2-Chloro-5-nitro-phenyl)-phenyl-methyl]-carbamoyl}-methyl)-4-fluoro-benzamide Prepared in analogy to example 1.1 from 4-fluoro-hippuric acid (CA [366-79-0]) and rac-C-(2-chloro-5-nitro-phenyl)-C-phenyl-methylamine (example 4.4).
MS (m/e): 442.3 (M+H).

Example 1.74

Preparation of rac-N-({[(2-Chloro-5-trifluoromethyl-phenyl)-phenyl-methyl]-carbamoyl}-methyl)-4-fluoro-benzamide Prepared in analogy to example 1.1 from 4-fluoro-hippuric acid (CA [366-79-0]) and rac-C-(2-chloro-5-trifluoromethyl-phenyl)-C-phenyl-methylamine hydrochloride (CA [13954-13-7]).
MS (m/e): 465.3 (M+H).

Example 1.75

Preparation of rac-4-Fluoro-N-({[(2-fluoro-phenyl)-phenyl-methyl]-carbamoyl}-methyl)-benzamide Prepared in analogy to example 1.1 from 4-fluoro-hippuric acid (CA [366-79-0]) and rac-C-(2-fluoro-phenyl)-C-phenyl-methylamine (CA [55095-24-4]).
MS (m/e): 381.4 (M+H, 16%).

Example 1.76

Preparation of rac-N-({[(4-Chloro-phenyl)-(3-trifluoromethyl-phenyl)-methyl]-carbamoyl}-methyl)-4-fluoro-benzamide Prepared in analogy to example 1.1 from 4-fluoro-hippuric acid (CA [366-79-0]) and rac-C-(4-chloro-phenyl)-C-(3-trifluoromethyl-phenyl)-methylamine hydrochloride (CA [49703-70-0]).
MS (m/e): 463.1 (MH⁻, 100%).

Example 1.77

Preparation of rac-4-Fluoro-N-({[(4-fluoro-phenyl)-(3-trifluoromethyl-phenyl)-methyl]-carbamoyl}-methyl)-benzamide Prepared in analogy to example 1.1 from 4-fluoro-hippuric acid (CA [366-79-0]) and rac-C-(4-fluoro-phenyl)-C-(3-trifluoromethyl-phenyl)-methylamine (example 4.5).
MS (m/e): 447.1 (MH⁻, 100%).

Example 1.78

Preparation of rac-4-Fluoro-N-({[p-tolyl-(3-trifluoromethyl-phenyl)-methyl]-carbamoyl}-methyl)-benzamide Prepared in analogy to example 1.1 from 4-fluoro-hippuric acid (CA [366-79-0]) and rac-C-p-tolyl-C-(3-trifluoromethyl-phenyl)-methylamine (example 4.6).
MS (m/e): 443.3 (MH⁻, 100%).

Example 1.79

Preparation of rac-4-Fluoro-N-({[(4-methoxy-phenyl)-(3-trifluoromethyl-phenyl)-methyl]-carbamoyl}-methyl)-benzamide

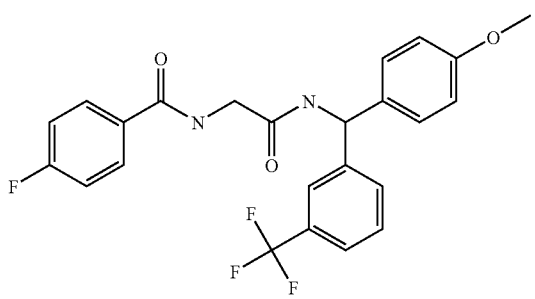

Prepared in analogy to example 1.1 from 4-fluoro-hippuric acid (CA [366-79-0]) and rac-C-(4-methoxy-phenyl)-C-(3-trifluoromethyl-phenyl)-methylamine (example 4.7).
MS (m/e): 459.2 (MH⁻, 100%).

Example 1.80

Preparation of rac-4-Fluoro-N-({[(4-trifluoromethoxy-phenyl)-(3-trifluoromethyl-phenyl)-methyl]-carbamoyl}-methyl)-benzamide

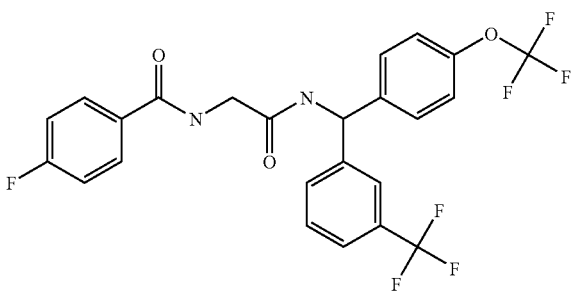

Prepared in analogy to example 1.1 from 4-fluoro-hippuric acid (CA [366-79-0]) and rac-C-(4-trifluoromethoxy-phenyl)-C-(3-trifluoromethyl-phenyl)-methylamine (example 4.8).
MS (m/e): 515.2 (M+H, 3%).

Example 1.81

Preparation of rac-4-Fluoro-N-{[(phenyl-thiophen-2-yl-methyl)-carbamoyl]-methyl}-benzamide

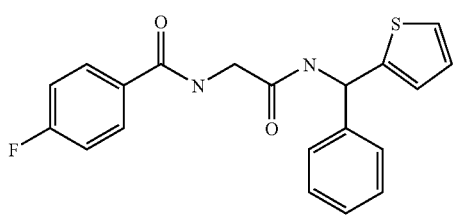

Prepared in analogy to example 1.1 from 4-fluoro-hippuric acid (CA [366-79-0]) and rac-C-phenyl-C-thiophen-2-yl-methylamine (CA [5693-42-5]).
MS (m/e): 367.1 (MH⁻, 100%).

Example 1.82

Preparation of rac-4-Fluoro-N-{[(phenyl-o-tolyl-methyl)-carbamoyl]-methyl}-benzamide

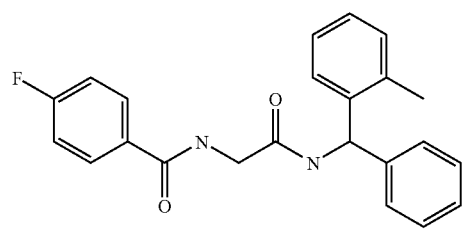

Prepared in analogy to example 1.1 from 4-fluoro-hippuric acid (CA [366-79-0]) and rac-C-phenyl-C-o-tolyl-methylamine (CA [2936-62-1]).
MS (m/e): 377.4 (M+H).

Example 1.83

Preparation of rac-4-Fluoro-N-{[(isothiazol-5-yl-phenyl-methyl)-carbamoyl]-methyl}-benzamide

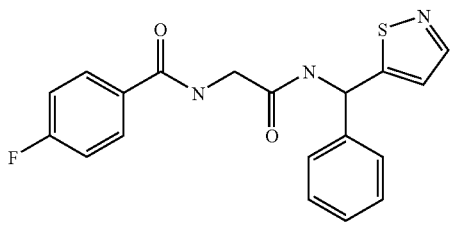

Prepared in analogy to example 1.1 from 4-fluoro-hippuric acid (CA [366-79-0]) and rac-C-isothiazol-5-yl-C-phenyl-methylamine hydrochloride (example 4.9).
MS (m/e): 368.1 (MH⁻, 100%).

Example 1.84

Preparation of rac-4-Fluoro-N-{[(phenyl-pyridin-4-yl-methyl)-carbamoyl]-methyl}-benzamide

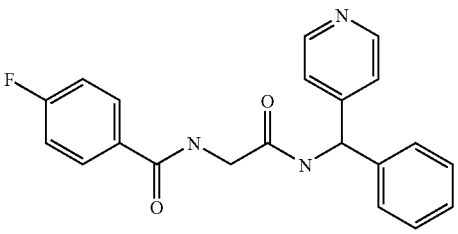

Prepared in analogy to example 1.1 from 4-fluoro-hippuric acid (CA [366-79-0]) and rac-C-phenyl-C-pyridin-4-yl-methylamine (CA [58088-57-6]).
MS (m/e): 364.1 (MH⁻, 100%).

Example 1.85

Preparation of rac-4-Fluoro-N-({[(3-fluoro-phenyl)-(3-trifluoromethyl-phenyl)-methyl]-carbamoyl}-methyl)-benzamide

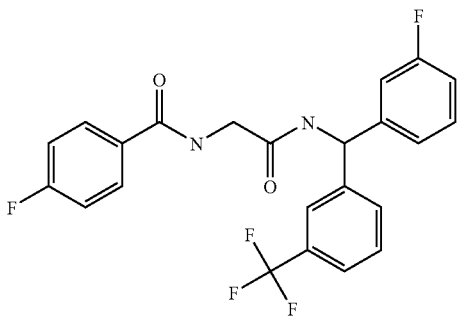

Prepared in analogy to example 1.1 from 4-fluoro-hippuric acid (CA [366-79-0]) and rac-C-(3-fluoro-phenyl)-C-(3-trifluoromethyl-phenyl)-methylamine hydrochloride (example 4.10).
MS (m/e): 447.1 (MH⁻, 100%).

Example 1.86

Preparation of 5-Methyl-thiophene-2-carboxylic acid ({[bis-(3-fluoro-phenyl)-methyl]-carbamoyl}-methyl)-amide

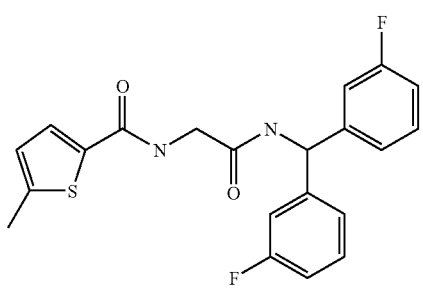

Prepared in analogy to example 1.12 from 2-amino-N-[bis-(3-fluoro-phenyl)-methyl]-acetamide (example 3.4) and 5-methyl-thiophene-2-carboxylic acid.
MS (m/e): 399.1 (MH⁻, 78%).

Example 1.87

Preparation of 3-Methyl-thiophene-2-carboxylic acid ({[bis-(3-fluoro-phenyl)-methyl]-carbamoyl}-methyl)-amide

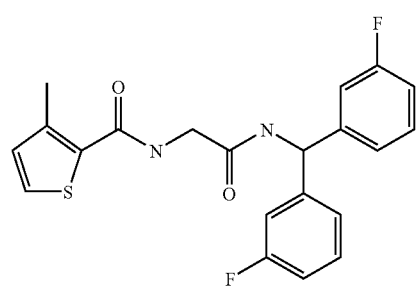

Prepared in analogy to example 1.12 from 2-amino-N-[bis-(3-fluoro-phenyl)-methyl]-acetamide (example 3.4) and 3-methyl-thiophene-2-carboxylic acid.
MS (m/e): 399.1 (MH⁻, 100%).

Example 1.88

Preparation of Cyclohexanecarboxylic acid ({[bis-(3-fluoro-phenyl)-methyl]-carbamoyl}-methyl)-amide

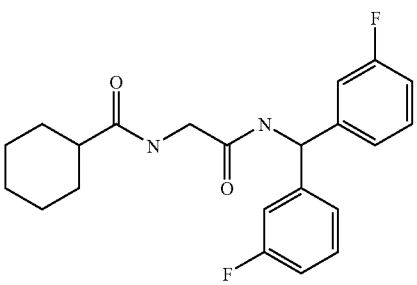

Prepared in analogy to example 1.12 from 2-amino-N-[bis-(3-fluoro-phenyl)-methyl]-acetamide (example 3.4) and cyclohexane-carboxylic acid.
MS (m/e): 385.2 (MH⁻, 100%).

Example 1.89

Preparation of rac-4-Fluoro-N-{[(phenyl-pyridazin-3-yl-methyl)-carbamoyl]-methyl}-benzamide

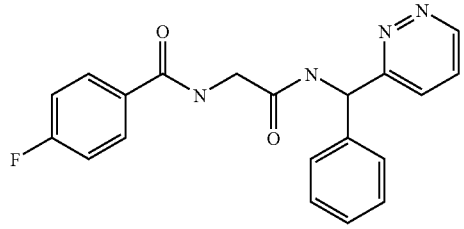

Prepared in analogy to example 1.1 from 4-fluoro-hippuric acid (CA [366-79-0]) and rac-C-phenyl-C-pyridazin-3-yl-methylamine (example 4.11).
MS (m/e): 363.3 (MH⁻, 100%).

Example 1.90

Preparation of N-({[Bis-(3-fluoro-phenyl)-methyl]-carbamoyl}-methyl)-2-chloro-3-trifluoromethyl-benzamide

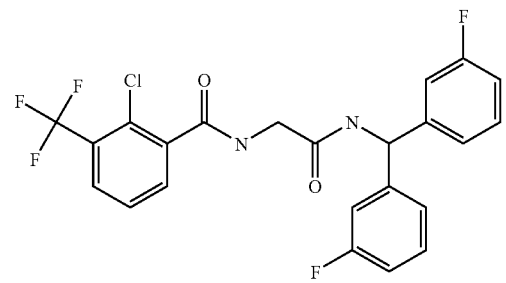

Prepared in analogy to example 1.12 from 2-amino-N-[bis-(3-fluoro-phenyl)-methyl]-acetamide (example 3.4) and 2-chloro-3-trifluoromethyl-benzoic acid.
MS (m/e): 481.1 (MH⁻, 100%).

Example 1.91

Preparation of rac-4-Fluoro-N-({[(3-fluoro-phenyl)-phenyl-methyl]-carbamoyl}-methyl)-benzamide

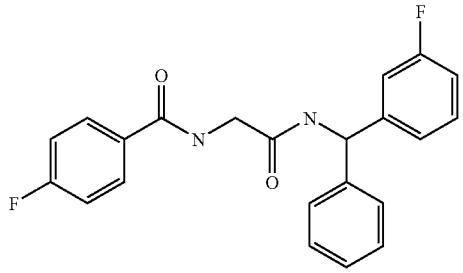

To rac-C-(3-fluoro-phenyl)-C-phenyl-methyl amine chloride (55095-25-5], 0.1 g) in DMF (2.0 mL) was added 4-(fluoro-benzoylamino)-acetic acid ([366-79-0], 0.075 g), Hünig's base (0.53 mL) and TBTU (0.123 g) and the reaction mixture was stirred overnight at room temperature. After such time water was added to the reaction mixture and the precipitate was isolated by filtration and washed with water yielding the title compound (0.11 g, 69%) as a white solid.
MS (m/e): 379.2 (MH⁻, 100%).

Example 1.92

Preparation of N-({[Bis-(3-fluoro-phenyl)-methyl]-carbamoyl}-methyl)-benzamide

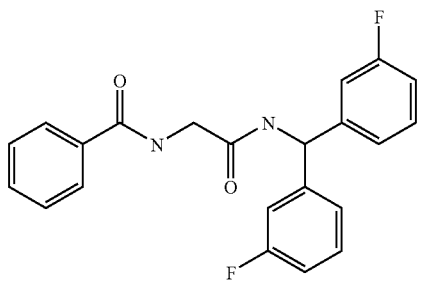

Prepared in analogy to example 1.12 from 2-amino-N-[bis-(3-fluoro-phenyl)-methyl]-acetamide (example 3.4) and benzoic acid.
MS (m/e): 379.2 (MH⁻, 100%).

Example 1.93

Preparation of N-({[Bis-(3-fluoro-phenyl)-methyl]-carbamoyl}-methyl)-3-fluoro-benzamide

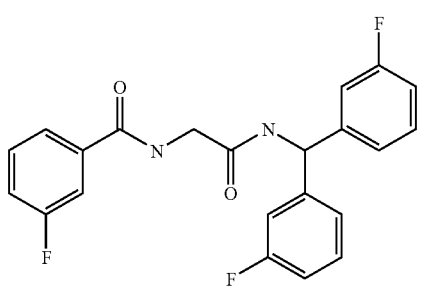

Prepared in analogy to example 1.12 from 2-amino-N-[bis-(3-fluoro-phenyl)-methyl]-acetamide (example 3.4) and 3-fluorobenzoic acid.
MS (m/e): 397.1 (MH⁻, 100%).

Example 1.94

Preparation of N-({[Bis-(3-fluoro-phenyl)-methyl]-carbamoyl}-methyl)-4-nitro-benzamide

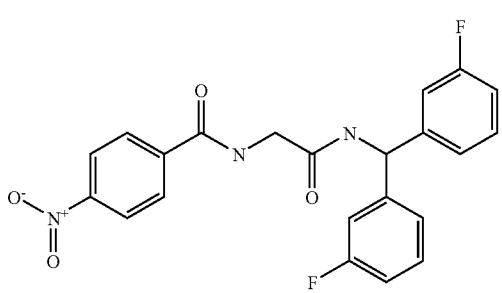

Prepared in analogy to example 1.12 from 2-amino-N-[bis-(3-fluoro-phenyl)-methyl]-acetamide (example 3.4) and 4-nitrobenzoic acid.
MS (m/e): 424.1 (MH⁻, 100%).

Example 1.95

Preparation of N-({[Bis-(3-fluoro-phenyl)-methyl]-carbamoyl}-methyl)-isonicotinamide

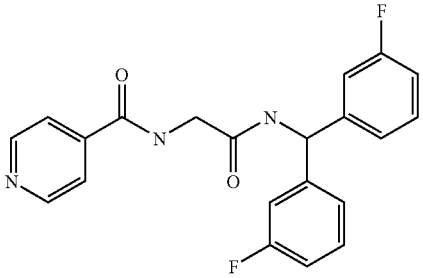

Prepared in analogy to example 1.12 from 2-amino-N-[bis-(3-fluoro-phenyl)-methyl]-acetamide (example 3.4) and isonicotinic acid.
MS (m/e): 380.2 (MH⁻, 100%).

Example 1.96

Preparation of Thiophene-2-carboxylic acid ({[bis-(3-fluoro-phenyl)-methyl]-carbamoyl}-methyl)-amide

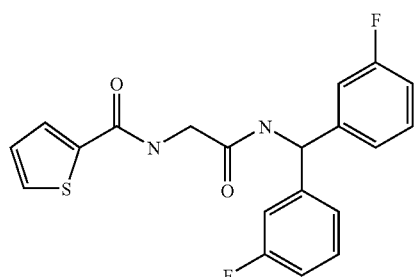

Prepared in analogy to example 1.12 from 2-amino-N-[bis-(3-fluoro-phenyl)-methyl]-acetamide (example 3.4) and thiophene-2-carboxylic acid.
MS (m/e): 385.1 (MH⁻, 100%).

Example 1.97

Preparation of 5-Nitro-thiophene-2-carboxylic acid ({[bis-(3-fluoro-phenyl)-methyl]-carbamoyl}-methyl)-amide

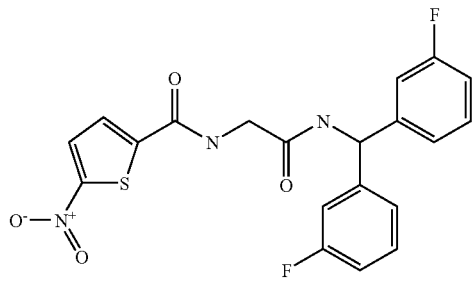

Prepared in analogy to example 1.12 from 2-amino-N-[bis-(3-fluoro-phenyl)-methyl]-acetamide (example 3.4) and 5-nitro-thiophene-2-carboxylic acid.
MS (m/e): 430.2 (MH⁻, 100%).

Example 1.98

Preparation of Thiophene-3-carboxylic acid ({[bis-(3-fluoro-phenyl)-methyl]-carbamoyl}-methyl)-amide

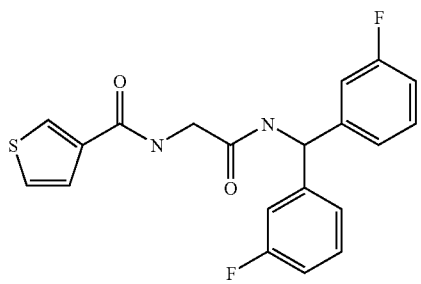

Prepared in analogy to example 1.12 from 2-amino-N-[bis-(3-fluoro-phenyl)-methyl]-acetamide (example 3.4) and thiophene-3-carboxylic acid.
MS (m/e): 385.1 (MH⁻, 100%).

Intermediates for Compounds of Formula II

Example 2.1

Preparation of [3-(4-Chloro-phenyl)-propionylamino]-acetic acid

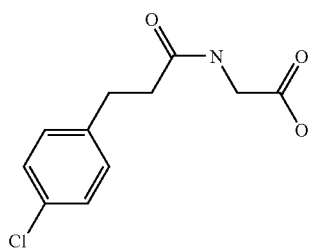

To a solution of 26 mmol sodium hydroxide in 7 ml water 8.7 mmol of glycine were added. The mixture was cooled in an ice-bath and a solution of 8.7 mmol 3-(4-chloro-phenyl)-propionyl chloride (CA [52085-96-8]) in 10 ml dioxane was slowly added over a period of 20 minutes. After stirring overnight at room temperature, the mixture was extracted with diethyl ether. The aqueous phase was acidified by addition of diluted hydrochloric acid and filtered. Trituration of the solid in diethyl ether yielded the title compound as a colorless solid. Yield=42%.

MS (m/e): 240.1 (MH⁻, 100%).

Example 2.2

Preparation of [3-(4-Methoxy-phenyl)-propionylamino]-acetic acid

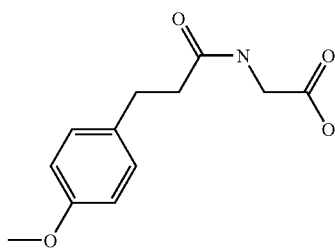

Prepared in analogy to example 2.1 from glycine and 3-(4-methoxy-phenyl)-propionyl chloride (CA [15893-42-2]).
MS (m/e): 236.1 (MH⁻, 100%).

Intermediates for Compounds of Formula XIV

Example 3.1

Preparation of 2-Amino-N-[(4-chloro-phenyl)-phenyl-methyl]-acetamide hydrochloride a) ({[(4-Chloro-phenyl)-phenyl-methyl]-carbamoyl}-methyl)-carbamic acid tert-butyl ester

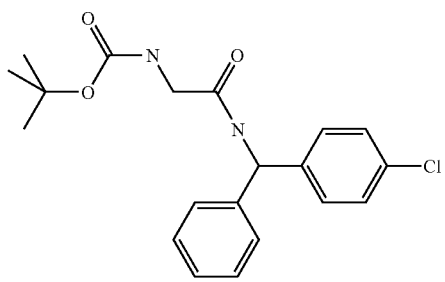

A suspension of 7.9 mmol C-(4-chloro-phenyl)-C-phenyl-methylamine hydrochloride (CA [5267-39-0]) in 100 ml acetonitrile was treated successively with 7.9 mmol N-tert.-butyloxycarbonyl glycine, 39 mmol DIPEA and 8.7 mmol TBTU. After stirring for 1 hour at room temperature, the mixture was concentrated. Chromatography (SiO$_2$; ethyl acetate/cyclohexane) yielded the title compound as a colorless solid. Yield=84%.

b) 2-Amino-N-[(4-chloro-phenyl)-phenyl-methyl]-acetamide hydrochloride

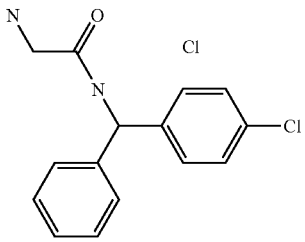

6.6 mmol ({[(4-Chloro-phenyl)-phenyl-methyl]-carbamoyl}-methyl)-carbamic acid tert-butyl ester were treated with 30 ml of a saturated solution of hydrogen chloride in diethyl ether. The mixture was stirred at room temperature for 1 hour. Removal of the diethyl ether in the rotatory evaporator yields the title compound as a colorless solid. Yield=100%.

MS (m/e): 273.0 (MH$^-$, 100%).

Example 3.2

Preparation of 2-Amino-N-[phenyl-(4-trifluoromethyl-phenyl)-methyl]-acetamide hydrochloride

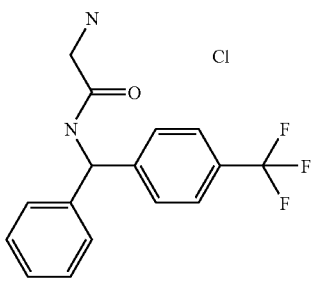

Prepared in analogy to example 3.1, starting from N-tert.-butyloxycarbonyl glycine and C-phenyl-C-(4-trifluoromethyl-phenyl)-methylamine hydrochloride (CA [49703-60-8]).

MS (m/e): 307.3 (MH$^-$, 100%).

Example 3.3

Preparation of 2-Amino-N-(phenyl-p-tolyl-methyl)-acetamide hydrochloride

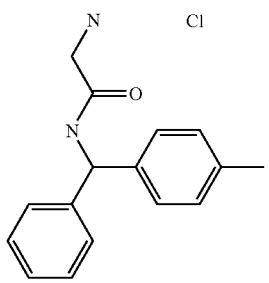

Prepared in analogy to example 3.1, starting from N-tert.-butyloxycarbonyl glycine and C-phenyl-C-p-tolyl-methylamine (CA [164362-05-4]).

MS (m/e): 255.2 (M+H, 100%).

Example 3.4

Preparation of 2-Amino-N-[bis-(3-fluoro-phenyl)-methyl]-acetamide hydrochloride

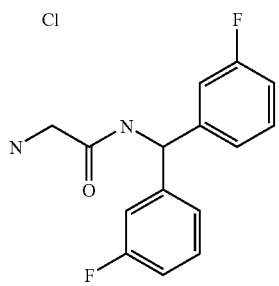

Prepared in analogy to example 3.1, starting from N-tert.-butyloxycarbonyl glycine and C,C-bis-(3-fluoro-phenyl)-methylamine (CA [261925-16-0]).

MS (m/e): 311.2 (M+H, 100%).

Intermediates for Compounds of Formula III

Example 4.1

Preparation of C,C-Bis-(4-trifluoromethyl-phenyl)-methylamine

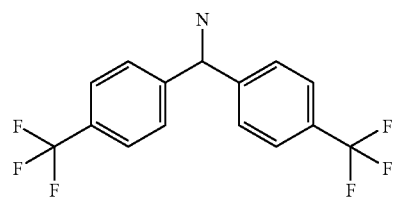

A suspension of 5 mmol magnesium-turnings in 10 ml diethyl ether was treated with 5 mmol 4-bromobenzotrifluoride to form the corresponding Grignard-reagent. This reagent was slowly added to a cooled solution of 5 mmol 4-(trifluoromethyl)benzonitrile in 10 ml of tetrahydrofuran at −70° C. After 1 hour at −70° C., the reaction mixture was stirred additional 2 hours at room temperature and then refluxed overnight. The resulting mixture was cooled again to 0° C. and diluted with 10 ml of methanol and 10 mmol sodium borohydride were added. After stirring for 2 hours at room temperature, the mixture was poured into 100 ml of 0.5 M aqueous hydrochloric acid and extracted with diethyl ether. The aqueous phase was adjusted to pH=10 by addition of diluted aqueous sodium hydroxide and extracted 3 times with dichloromethane. Chromatography (SiO$_2$; dichloromethane/methanol) yielded the title compound as a slightly brown foam.

Yield=2%.
MS (m/e): 320.3 (M+H, 100%).

Example 4.2

Preparation of C-(2,4-Dichloro-phenyl)-C-phenyl-methylamine

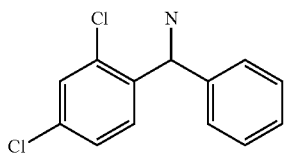

Prepared in analogy to example 4.1, starting from phenyl-magnesium bromide and 2,4-dichloro benzonitrile. Yield=56%.

MS (m/e): 235.0 (M+NH3, 100%)

Example 4.3

Preparation of C-(3,5-Difluoro-phenyl)-C-phenyl-methylamine hydrochloride

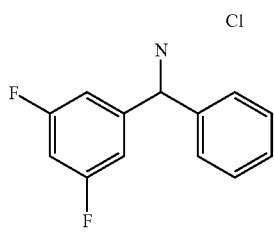

Step 1: (3,5-Difluoro-phenyl)-phenyl-methanone oxime

To 3,5-difluorobenzophenone (2.5 g) in ethanol (30 mL) was added hydroxylamine hydrochloride (3 eq) and sodium-carbonate (3 eq). The reaction mixture was stirred at reflux for 4 hours and then allowed to cool down to room temperature. The precipitate was then isolated by filtration and washed with water to yield the title compound as a white solid (m.p.=91-93° C., Yield=89%), reflux, 4 h MS (m/e): 234.3 (M+H),

Step 2: C-(3,5-Difluoro-phenyl)-C-phenyl-methylamine hydrochloride

To (3,5-difluoro-phenyl)-phenyl-methanone oxime (1.0 g) in methanol (40 mL) was added Palladium-C (Degussa E101N, 5%) and the reaction mixture was stirred under a hydrogen atmosphere at room temperature for 2 hours. After such time, the catalyst was removed and the filtrate concentrated in vacuo. The residue was dissolved in 10 mL of diethylether and the corresponding salt was formed by addition of a 10M HCl solution in diethyl ether. After allowing to stir for an extra 5 minutes, the fine precipitate was isolated by filtration to yield the title compound as a white powder (0.944 g, 86.1%, m.p.: 290-295° C., (EI): 219.1 (M)

Example 4.4

Preparation of C-(2-Chloro-5-nitro-phenyl)-C-phenyl-methylamine

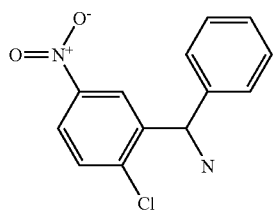

This compound was prepared by the method of Dejaegher et al., Synlett 2002, 113 (see Scheme 4).

Example 4.5

Preparation of C-(4-Fluoro-phenyl)-C-(3-trifluoromethyl-phenyl)-methylamine hydrochloride

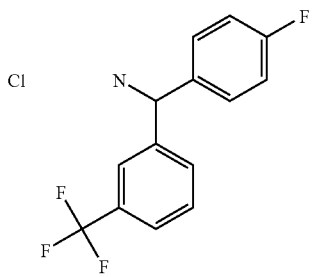

Under an Argon atmosphere, 3-trifluoromethylbenzyl magnesium bromide (20.3 mL) was added dropwise to a 4-fluoro-benzonitrile (2.0 g) solution in diethylether. The reaction mixture was then refluxed for 2 hours and allowed to cool before adding the lithium aluminium hydride solution (1M, 10.8 mL) in a dropwise manner. The reaction was then refluxed overnight and then allowed to cool to room temperature. 3 ml of ethyl acetate was added, followed by 4 ml of water. The reaction mixture was then filtered and the product was precipitated from the filtrate with the addition of concentrated hydrochloric acid in ether. The title compound was isolated by filtration, and dried under vacuum to yield the title compound as a white solid (1.47 g, 30%).

MS (m/e) 255.2 (2%), 254.2 (11), 235.1 (100%)

1H NMR (CDCl3, 300 MHz) 9.41 (3H, s, NH), 8.03 (1H, s), 7.89-7.87, (1H, d, J=7.6 Hz), 7.76-7.70 (1H, t, J=7.8 Hz), 7.70-7.64 (1H, t, J=9.5 Hz), 7.67-7.63 (H, t, J=8.5 Hz), 7.32-7.26 (2H, t, J=8.9 Hz).

Example 4.6

Preparation of
C-p-Tolyl-C-(3-trifluoromethyl-phenyl)-methylamine hydrochloride

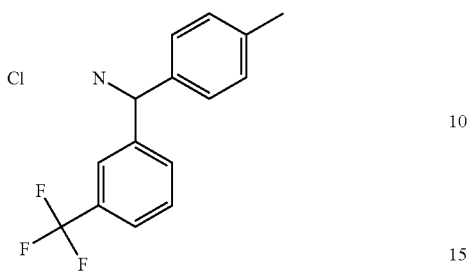

Prepared in analogy to example 4.5, starting from 3-trifluoromethylphenylmagnesium bromide and 4-methyl benzonitrile.
MS (m/e): 250.1 (2%), 249.1 (100%)

Example 4.7

Preparation of C-(4-Methoxy-phenyl)-C-(3-trifluoromethyl-phenyl)-methylamine hydrochloride

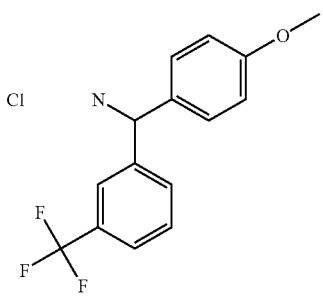

Prepared in analogy to example 4.5, starting from 3-trifluoromethylphenylmagnesium bromide and 4-methoxybenzonitrile.
MS (m/e): 250.1 (2%), 249.1 (100%)

Example 4.8

Preparation of C-(4-Trifluoromethoxy-phenyl)-C-(3-trifluoromethyl-phenyl)-methylamine; hydrochloride

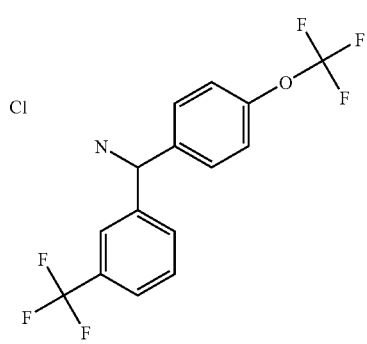

Prepared in analogy to example 4.5, starting from 3-trifluoromethylphenylmagnesium bromide and 4-trifluoromethoxybenzonitrile.
MS (m/e): 267.2 (2%), 266.2 (24), 265.2 (100%)

Example 4.9

Preparation of
C-Isothiazol-5-yl-C-phenyl-methylamine hydrochloride

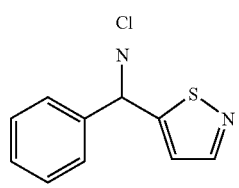

Step 1: Phenyl-thiazol-2-yl-methanone

This compound was prepared in analogy to the method described by A. J. Layton et al., J. Chem. Soc. (C), 1968, 611.

Step 2: Phenyl-thiazol-2-yl-methanone oxime

To Phenyl-thiazol-2-yl-methanone (0.5 g) in ethanol (6 mL) was added hydroxylamine hydrochloride (3 eq) and sodiumcarbonate (3 eq). The reaction mixture was stirred at reflux overnight and then allowed to cool down to room temperature. The precipitate was then isolated by filtration and washed with water to yield the title compound as a light grey solid. MS (m/e): 207.1 (5), 206.1 (10), 205.1 (100% M+H+)

Step 3: C-Isothiazol-5-yl-C-phenyl-methylamine hydrochloride

To a solution of Phenyl-thiazol-2-yl-methanone oxime (0.1 g) in 1,2-dimethoxyethane (1.0 mL), was added NaBH4 (0.078 g). TiCl4 (1.03 mL) was then slowly added under nitrogen atmosphere at 0° C. The mixture was warmed up to room temperature and stirred for 24 hours. Then 10 mL of ice cold water was added, the solution was alkalised with ammonium hydroxide solution, and extracted with ethyl acetate. The organic layer was washed with a saturated solution of NaCl, dried over Na2SO4, and evaporated under reduced pressure. The product was dissolved in diethylether and filtered. The product was crashed out from the filtrate by addition of HCl/diethylether. The product was dried under high vacuum at 40° C. to yield the title compound (0.041 g, 37%).
MS (m/e): 176.2 (5%), 175.3 (10), 174.2 (100%)

Example 4.10

Preparation of C-(3-Fluoro-phenyl)-C-(3-trifluoromethyl-phenyl)-methylamine hydrochloride

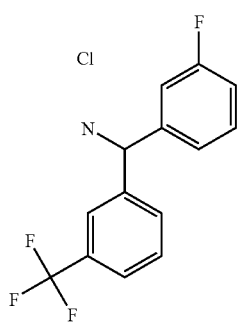

Prepared in analogy to example 4.5, starting from 3-trifluoromethylphenylmagnesium bromide and 3-fluoro-benzonitrile.

MS (m/e): 254.2 (11%), 253.1 (100%)

Example 4.11

Preparation of
C-Phenyl-C-pyridazin-3-yl-methylamine
hydrochloride

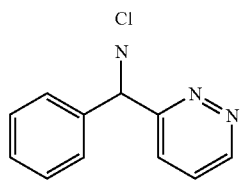

Step 1: Phenyl-pyridazin-3-yl-methanone oxime

Phenyl-pyridazin-3-yl-methanone oxime was formed from Phenyl-pyridazin-3-yl-methanone [60906-52-7] in a similar way as phenyl-thiazol-2-yl-methanone oxime (Example 4.9) was.

MS (EI) 201.2 (15%), 200.1 (98 M+H+), 183.1 (12), 182.1 (100%)

Step 2: C-Phenyl-C-pyridazin-3-yl-methylamine hydrochloride

Bis-(3-fluoro-phenyl)-methanone oxime (0.2 g) was dissolved in methanol (8 mL). Palladium-C (0.043 g) was added to form a suspension and the air within the flask was evacuated. Hydrogen gas was added via a balloon for 4 hours until the reaction was complete by tlc. The catalyst was filtered off and the filtrate was concentrated under reduced pressure. The product formed was dissolved in diethylether filtered and crashed out of the filtrate with the addition of HCl in diethylether. The solid product was filtered of and dried under high vacuum at 40° C. for 5 hours to yield the title compound (0.134 g, 60%).

MS (m/e): 173.2 (9%), 171.2 (3), 170.2, (14%), 169.1 (100%)

The invention claimed is:

1. A compound of formula I

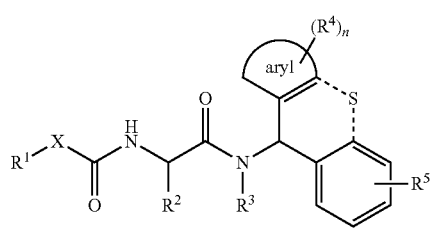

wherein

is a 5 or 6-membered aromatic ring;

$R^1$ is cycloalkyl or is aryl, which is unsubstituted or substituted by 1 to 3 substituents selected from the group consisting of halogen, lower alkyl, lower alkyl substituted by halogen, lower alkoxy, lower alkoxy substituted by halogen, —C(O)-lower alkyl, —S(O)$_2$-lower alkyl, nitro and cyano;

$R^2$ is hydrogen or lower alkyl;

$R^3$ is hydrogen or lower alkyl;

$R^4$ is halogen, lower alkyl substituted by halogen, lower alkoxy substituted by halogen or nitro;

$R^5$ is hydrogen, halogen, or lower alkyl substituted by halogen;

X is a bond, —(CH$_2$)$_m$—, —CH$_2$O— or —CH$_2$NH—;

The dotted line denotes an optional bond;

n is 1 or 2; and m is 1, 2 or 3;

or a pharmaceutically acceptable acid addition salt thereof with the proviso that the dotted line is not a bond.

2. The compound of claim 1, wherein X is a bond.

3. The compound of claim 2, wherein

is phenyl, monosubstitued by a substituent selected from the group consisting of halogen and lower alkyl substituted by halogen, and $R^1$ is an aryl group, unsubstituted or substituted by fluoro, cyano or nitro.

4. The compound of claim 3, selected form the group consisting of rac-N-({[(4-chloro-phenyl)-phenyl-methyl]-carbamoyl}-methyl)-4-fluoro-benzamide, rac-N-({[phenyl-(3-trifluoromethyl-phenyl)-methyl]-carbamoyl}-methyl)-benzamide, rac-4-fluoro-N-({[phenyl-(3-trifluoromethyl-phenyl)-methyl]-carbamoyl}-methyl)-benzamide, rac-4-cyano-N-({[phenyl-(3-trifluoromethyl-phenyl)-methyl]-carbamoyl}-methyl)-benzamide, N-[(benzhydryl-carbamoyl)methyl]-4-fluoro-benzamide, rac-N-({[(3-chloro-phenyl)-phenyl-methyl]-carbamoyl}-methyl)-4-fluoro-benzamide, and rac-4-fluoro-N-({[(4-fluoro-phenyl)-phenyl-methyl]-carbamoyl}-methyl)-benzamide.

5. The compound of claim 3, selected form the group consisting of

N-({[bis-(3-fluoro-phenyl)-methyl]-carbamoyl}-methyl)-4-fluoro-benzamide, rac-N-({[(3,5-difluoro-phenyl)-phenyl-methyl]-carbamoyl}-methyl)-4-fluoro-benzamide, rac-N-({[(4-chloro-phenyl)-(3-trifluoromethyl-phenyl)-methyl]-carbamoyl}-methyl)-4-fluoro-benzamide, rac-4-fluoro-N-({[(4-fluoro-phenyl)-(3-trifluoromethyl-phenyl)-methyl]-carbamoyl}-methyl)-benzamide, rac-4-fluoro-N-({[(3-fluoro-phenyl)-(3-trifluoromethyl-phenyl)-methyl]-carbamoyl}-methyl)-benzamide, and N-({[bis-(3-fluoro-phenyl)-methyl]-carbamoyl}-methyl)-4-nitro-benzamide.

6. The compound of claim 1, wherein X is —(CH$_2$)$_m$—.
7. The compound of claim 1, wherein X is —CH$_2$O—.
8. The compound of claim 1, wherein X is —CH$_2$NH—.
9. The compound of claim 1, wherein n is 1.
10. The compound of claim 1 wherein aryl is phenyl, unsubstituted or substituted by 1 to 3 substituents selected from the group consisting of halogen, lower alkyl, and lower alkyl substituted by halogen.
11. The compound of claim 1, wherein X is a bond, aryl is phenyl, unsubstituted or substituted by 1 to 3 substituents selected from the group consisting of halogen, lower alkyl, lower alkyl substituted by halogen, lower alkoxy, lower alkoxy substituted by halogen, C(O)-lower alkyl, S(O)$_2$-lower alkyl, nitro, and cyano; and n is 1.
12. The compound of claim 1, wherein R$^3$ is H.
13. The compound of claim 1, wherein R$^3$ is methyl.
14. A pharmaceutical composition comprising a compound of formula I

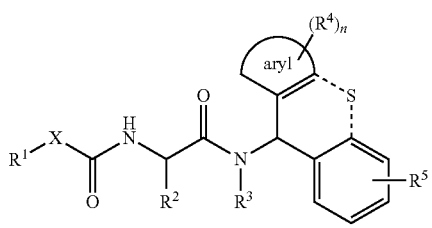

wherein

is a 5 or 6-membered aromatic ring;

R$^1$ is cycloalkyl or is aryl, which is unsubstituted or substituted by 1 to 3 substituents selected from the group consisting of halogen, lower alkyl, lower alkyl substituted by halogen, lower alkoxy, lower alkoxy substituted by halogen, —C(O)-lower alkyl, —S(O)$_2$-lower alkyl, nitro and cyano;

R$^2$ is hydrogen or lower alkyl;

R$^3$ is hydrogen or lower alkyl;

R$^4$ is halogen, lower alkyl substituted by halogen, lower alkoxy substituted by halogen or nitro;

R$^5$ is hydrogen, halogen, or lower alkyl substituted by halogen;

X is a bond, —(CH$_2$)$_m$—, —CH$_2$O— or —CH$_2$NH—;

The dotted line denotes an optional bond;

n is 1 or 2; and m is 1, 2 or 3;

or a pharmaceutically acceptable acid addition salt thereof with the proviso that the dotted line is not a bond and a pharmaceutically acceptable carrier.

* * * * *